US007557083B2

(12) United States Patent
Martin et al.

(10) Patent No.: US 7,557,083 B2
(45) Date of Patent: Jul. 7, 2009

(54) GASTROKINES AND DERIVED PEPTIDES INCLUDING INHIBITORS

(75) Inventors: Terence E. Martin, Chicago, IL (US); F. Gary Toback, Chicago, IL (US); Thomas C. Powell, Bratenahl Place, OH (US); Kan Agarwal, Chicago, IL (US); Miriana Choudhary, legal representative, Chicago, IL (US)

(73) Assignee: The University of Chicago, Chicago, IL (US)

( * ) Notice: Subject to any disclaimer, the term of this patent is extended or adjusted under 35 U.S.C. 154(b) by 526 days.

(21) Appl. No.: 10/473,524

(22) PCT Filed: Mar. 29, 2002

(86) PCT No.: PCT/US02/10148

§ 371 (c)(1), (2), (4) Date: Oct. 21, 2004

(87) PCT Pub. No.: WO02/092758

PCT Pub. Date: Nov. 21, 2002

(65) Prior Publication Data

US 2005/0065328 A1 Mar. 24, 2005

(51) Int. Cl.
*A61K 38/17* (2006.01)
*A61K 38/00* (2006.01)
*C07K 11/00* (2006.01)
*C07K 14/00* (2006.01)

(52) U.S. Cl. ............................ 514/12; 514/14; 514/13; 514/2; 530/300; 530/350

(58) Field of Classification Search ....................... None
See application file for complete search history.

(56) References Cited

U.S. PATENT DOCUMENTS

| | | | |
|---|---|---|---|
| 5,644,026 | A | 7/1997 | Yamaguchi et al. |
| 6,670,119 | B1 | 12/2003 | Yoshikawa et al. |
| 6,734,289 | B2 | 5/2004 | Martin et al. |

FOREIGN PATENT DOCUMENTS

| | | | |
|---|---|---|---|
| EP | 0972830 A | | 1/2000 |
| EP | 0972830 A1 | | 1/2000 |
| WO | WO 98/37187 A1 | | 8/1998 |
| WO | WO 99/07840 | | 2/1999 |
| WO | WO 00/00610 | | 1/2000 |
| WO | WO 00/43781 A2 | | 7/2000 |
| WO | WO 00/73348 | | 12/2000 |
| WO | WO 02/078640 A2 | | 10/2002 |

OTHER PUBLICATIONS

Yoshikawa et al., (2000) Isolation of two novel genes, down-regulated in gastric cancer. Japanese Journal of Cancer Research, Japanese Cancer Association, Tokyo, JP, vol. 91, No. 5, 459-463.

Database EMBL (2000), Human signal peptide containing protein, Accession No. AAY87272.

Database EMBL (2001), Accession No. AX055699.

Aithal, N.H., et al. (1994) "Glyceraldehyse-3-phosphate Dehydrogenase Modifier Protein is Associated with Microtubules in Kidney Epithelial Cells." *AM. J. Physiol.* 266:F612-619.

Altschul, S.F., et al. (1997) "Gapped BLAST and PSI-BLAST: a New Generation of Protein Database Search Programs." *Nuc. Acids Res.* 25 (17):3389-3402.

Baczako, K et al. (1995) "Lectin-Binding Properties of the Antral and Body Surface Mucosa in the Human Stomach—Are Difference Relevant for Helicobacter Pylon Affinity?" *J. Pathol* 176:77-86.

Blaser, M.J. (1987) "Gastric *Campylobacter*-like Organisms, Gastritis, and Peptic Ulcer Disease." *Gastroenterol.* 93:371-383.

Boman, H.G. (1995) "Peptide Antibiotics and Their Role in Innate Immunity." *Ann. Rev. Immunol.* 13:61-92.

Cohen, G.B., et al. (1995) "Modular Binding Domains in Signal Transduction Proteins." *Cell* 80:237-248.

Cregg, J.M., et al. (1993) "Recent Advances in the Expression of Foreign Genes in *Pichia pastoris.*" *Bio/Technol.* 11:905-910.

Dignass, A.U., et al. (1998) "Adenine Nucleotides Modulate Epithelial Wound Healing In Vitro." *Eur. J. Clin. Invest.* 28:554-561.

Falk, P., et al. (1993) "An In vitro Adherence Assay Reveals That *Helicobacter Pylori* Exhibits Cell Lineage-Specific Tropism in the Human Gastric Epithelium." *Proc. Nat. Acad. Sci. USA* 90:2035-2039.

Goodwin, C.S., et al., (1986) "*Campylocbacter pyloridis*, Gastritis, and Peptic Ulceration." *J. Clin. Pathol.* 39:353-356.

Hasty, P., et al. (1991) "The Length of Homology Required for Gene Targeting in Embryonic Stem Cells." *Mol. Cell. Biol.* 11:5586-5591.

Houston, M.E., et al. (1996) "Lactam Bridge Stabilization of α-Helices: The Role of Hydrophobicity in Controlling Dimeric versus Monomeric α-Helices." *Biochem.* 35:10041-10050.

Janknecht, R., et al. (1991) "Rapid and Efficient Purification of Native Histidine-Tagged Protein Expressed by Recombinant Vaccinia Virus." *Proc. Nat. Acad. Sci. USA* 88:8972-8976.

Jeon, C.J., et al. (1994) "The Transcription Factor TFIIS Zinc Ribbon Dipeptide Asp-Glu is Critical for Stimulation of Elongation and RNA Cleavage by RNA Polymerase II." *Proc. Nat. Acad. Sci. USA* 91:9106-9110.

Johnson, F.R. and McMinn, R.M.H. (1970) "Microscopic Structure of Pyloric Epithelium of the Cat." *J. Anat.* 107:67-86.

(Continued)

*Primary Examiner*—Marianne P Allen
*Assistant Examiner*—Regina M DeBerry
(74) *Attorney, Agent, or Firm*—Barnes & Thornburg LLP; Alice O. Martin

(57) ABSTRACT

A novel group of gastrokines called Gastric Antrum Mucosal Protein is characterized. A member of the group is designated AMP-18. AMP-18 genomic DNA, cDNA and the AMP-18 protein are sequenced for human, mouse and pig. The AMP-18 protein and active peptides derived from it are cellular growth factors. Surprisingly, peptides capable of inhibiting the effects of the complete protein, are also derived from the AMP-18 protein. Control of mammalian gastro-intestinal tissues growth and repair is facilitated by the use of the proteins, making the proteins candidates for therapies.

1 Claim, 26 Drawing Sheets

OTHER PUBLICATIONS

Kartha, S. and Toback, F.G. (1985) "Purine Nucleotides Stimulate DNA Synthesis in Kidney Epithelial Cells in Culture." *Am. J. Physiol.* 249:F967-F972.

Lacy, E.R. (1998) "Epithelial Restitution in the Gastrointestinal Tract." *J. Clin. Gastroenterol.* 10(Suppl 1):s72-s77.

Lieski, J.C., et al. (1994) "Renal Epithelial Cells Rapidly Bind and Internalize Calcium Oxalate Monohydrate Crystals." *Proc. Natl. Acad. Sci. USA* 91:6987-6991.s.

Lieske, J.C., et al. (1997) "Adhesion of Hydroxyapatite Crystals to Anionic Sites on the Surface of Renal Epithelial Cells." *Am. J. Physiol.* F224-F233.

Mansour, S., et al. (1988) "Disruption of the Proto-Oncogene *int-2* in Mouse Embryo-Derived Stem Cells: A General Strategy for Traget-ing Mutations to Non-Selectable Genes." *Nature* 336:348-352.

Moore, K.S., et al. (1991) "Antimicrobial Peptides in the Stomach of *Xenpus laevis." J. Biol. Chem.* 266 (2a):19851-19857.

Nguyen, J.T., et al. (1998) "Exploiting the Basis of Proline Recognition by SH3 and WW Domains: Design of N-Substituted Inhibitors." *Science* 282:2088-2092.

Nomura, A., et al. (1991) "*Helicobacter Pylori* Infection and Gastric Carcinoma Among Japanese Americans in Hawaii." *N. Engl. J. Med.* 325 (16):1132-1136.

Nusrat, A., et al. (1992) "Intestinal Epithelial Restitution." *J. Clin. Invest.* 89:1501-1511.

Park, C.B., et al. (1997) "A Novel Antimicrobial Peptide From the Loach, *Misgurnus anguillicaudatus." FEBS Lett.* 411:173-178.

Parsonnet, J., et al. (1991) "*Helicobacter pylori* Infection of the Risk of Gastric Carcinoma." *N. Engl. J. Med.* 325 (16):1127-1131.

Podolsky, D.K. (1997) Healing the Epithelium: Solving the Problem from Two Sides. *J. Gastroenterol.* 32:122-126.

Powell, C.T. (1987) "Characterization of a Novel Messenger RNA and Immunochemical Detection of its Protein from Porcine Gastric Mucosa." *Ph.D. Dissertation*; The University of Chicago.

Quaroni, A., et al. (1979) "Epithelioid Cell Cultures From Rat Small Intestine." *J. Cell Biol.* 80:248-265.

Romanos, M.A. et al. (1992) "Foreign Gene Expression in Yeast: a Review" *Yeast* 8:423-488.

Rotimi, V.O., et al. (1990) "Acidity and Intestinal Bacteria: an In-Vitro Assessment of the Bactericidal Activity of Hydrochloric Acid on Intestinal Pathogens." *Afr. J. Med. med. Sci.* 19:275-280.

Sands, B.E. and Podolsky, D.K. (1996) "The Trefoil Peptide Family." *Ann. Rev. Physiol.* 58:253-273.

Schlessinger, J. and Ullrich, A. (1992) "Growth Factor Signaling by Receptor Tyrosine Kinases." *Neuron* 9:383-391.

Sears, I.B., et al. (1998) "A Versatile Set of Vectors for Constitutive and Regulated Gene Expression in *Pichia pastoris." Yeast* 14: 783-790.

Segarini, P.R., et al. (1987) "Membrane Binding Characteristics of Two Forms of Transforming Growth Factor-β" *J. Biol. Chem.* 262 (30):14655-14662.

Smith, D.B. and Johnson, K.S. (1988) "Single-Step Purification of Polypeptides Expressed in *Escherichia coli* as fusions with Glutathione *S*-transferase." *Gene* 67:31-40.

Toback, F.G. (1980) "Induction of Growth in Kidney Epithelial Cells in Culture by $Na^+$." *Proc. Nat. Acad. Sci.* 77 (11):6654-6656.

Waltz, S.E. (1997) "Functional Characterization of Domains Contained in Hepatocyte Growth Factor-like Protein" *The Journal of Biological Chemistry* vol. 272, No. 48: 30526-30537.

Yarden, Y. and Ullrich, A. (1988) "Molecular Analysis of Signal Transduction by Growth Factors." *Biochemistry* 27:3113-3119.

Yoo, O.J. et al. (1982) "Molecular Cloning and Nucleotide Sequence of Full-Length cDNA Coding for Porcine Gastrin." *PNAS* 79:1049-1053.

Yoshikawa, Y., et al. (2000) "Isolation of Two Novel Genes, Down-regulated in Gastric Cancer." *Jap. J, Cancer Res.* 91:459-463.

Clackson et al., "A Hot Spot of Binding Energy in a Hormone-Receptor Interface," *Science*, 267, 383-386 (1995).

Database Biosis: Walsh-Reitz et al., "Accumulation of Specific Tight and Adherens Junction Proteins is Stimulated by Antrum Mucosal Protein-18 in Colonic Epithelial Cells in Culture and Mouse In Vivo," Database Accession No. PREV200300571862, Abstract (2003).

Database EMBL (2001): "Human PRO1005 (UNQ489) Protein Sequence SEQ ID No. 211," Accession No. AAB65209.

Database EMBL (2001): "Mus Musculus Adult Male Stomach cDNA, RIKEN Full-Length Enriched Library, Clone: 2210420L15 Product: Weakly Similar to CA11 Protein [*Homo sapiens*], Full Insert Sequence," Accession No. AK008990.

Huang et al., "Transforming Growth Factor Beta Peptide Antagonists and Their Conversion to Partial Agonists," *The Journal of Biological Chemistry*, 272: (43), 27155-27159 (1997).

Kawai et al., "Functional Annotation of a Full-Length Mouse cDNA Collection," *Nature*, 409, 685-690 (2001).

Martin et al., "A Novel Mitogenic Protein That is Highly Expressed in Cells of the Gastric Antrum Mucosa," *American Journal of Physiology: Gastrointestinal and Liver Physiology*, 285: (2), G332-G343 (2003).

Schmassmann et al., "Roles of Hepatocyte Growth Factor and Its Receptor Met During Gastric Ulcer Healing in Rats," *Gastroenterology*, 113, 1858-1872 (1997).

Tarnawski, "Cellular and Molecular Mechanisms of Ulcer Healing," *Drugs of Today*, 33: (10), 697-707 (1997).

Toback et al., "Peptide Fragments of AMP-18, A Novel Secreted Gastric Antrum Mucosal Protein, Are Mitogenic and Motogenic," *American Journal of Physiology: Gastrointestinal and Liver Physiology*, 285: (2), G344-G353 (2003).

1 AGCTTTATAA CCATGTGATC CCATCTTATG GTTTCAATCC ATGCACAGGA

51 GGAAAATTGT GGGCACGAAG TTTCCAAAGG GAAAATTTAT AGATTGGTAG

101 TTAATGAAAT ACAGTTTTCC TCCTTGGCAA ATTTAATTTA CTAGCTTCAC

151 TGTATAGGAA AAAGCAGGAA AAAAATTAAA ACCAACTCAC CTCCAAACCT

201 GTTTTGAGCT TTTACTTGTC TGCCCAATTG ATAGTTTCTA CTCTCTGCTT

251 TTGATGAAAA TATTTTTTAT TATTTTAATG TAACTTCTGA AAACTAAATT

301 ATCTAGAAGC AAATAAAAAG ATATTGCTTT TATAGTTCCC AGAAGGAAAA

351 AACAAACACT AGGAAAGTTC TATCTATCAG ATGGGGGAGA TGTGATGGAG

401 GCAGTGATAT TTGAGCTGAG CCTTGAACAA TGAACAGGAG TCTACCAAGC

451 GAGAGGCTAG CGGGTGGCCC TCAAGATAAA ACAACAGCAT GTACAAAGGC

501 ATGGAGACAT ACACATCTTG ACTCTTCCAG GAATGGTGGG AACGCTGGTG

551 GAGCTAGAAT GTAGGTACAT AGCATAAAGT GGCAGACGGG AAGCCTTTGG

601 AAATCTTATT ACATAGGACC CTGGATGCCA TTCCAATGAC TTTGAATTTT

651 CTGTAGGCTG CCAGCGAAAT TTCCAAGCGT GATAGAGTCA TGTCTATCTA

701 TGCACTTCAG AAAGACAACC TCAGGGTTAA TGAAGAAAAT GCATTGGAAT

751 ATAAGAAACT GGTGACCAGA GTGATCAATT GCATGACTGT TGTGAAAGTC

801 CAGGTGAGGG GAGCTGTGGG CAAGGTCAGA GTTGAGAGGC ATTTCAGAGA

851 TAAAATGACA GTAACTAAGT AGATGTCAGG CTGAGAAGAA AGGGCTGTAC

901 CAGATATATG GTGCTATCAT TAAGTGAGCT CAACATTGCA GAAAAGGGGT

951 AGGTTTGGTG GGAGTTGCTC ACAAAACATG TTTAGTCTAA GCAAAACCAT

1001 TGCCATGGGC TCAGATAAAA GTTAAGAAGT GGAAACCATT CCTACATTCC

1051 TATAGGAGCT GCTATCTGGA AGGCCTAGTA TACACGTGGC TTTTCAGCTG

1101 TGATTTTGTT TGATTTTAGG GATTATTCTT TTTCTGAATC TGAGCAATGT

FIG. 1

1151 TAGCGTGTAA AATACTCACA CCCACAGCTT TGACTGGGTG AGAAGTTATC

1201 ATAAATCATA TTGAGTTTGT TGTGATACCT TCAGCTTCAA CAAGTGATGA

1251 GTCAGGTCAA CTCCATGTGA AAGTTCCTTG CTAAGCATGC AGATATTCTG

1301 AAAGGTTTCC TGGTACACTG GCTCATGGCA CAGATAGGAG AAATTGAGGA

1351 AGGTAAGTCT TTGACCCCAC CTGATAACAC CTAGTTTGAG TCAACCTGGT

1401 TAAGTACAAA TATGAGAAGG CTTCTCATTC AGGTCCATGC TTGCCTACTC

1451 CTCTGTCCAC TGCTTTCGTG AAGACAAGAT GAAGTTCACA GTGAGTAGAT

1501 TTTTCCTTTT GAATTTACCA CCAAATGATT GGAGACTGTC AATATTCTGA

1551 GATTTAGGAG GTTTGCTTCT TATGGCCCCA TCATGGAAAG TTTGTTTTAA

1601 AAAAATTCTC TCTTCAAACA CATGGACACA GAGAGGGGAA CAACACACAC

1651 CAGGTCCTGT TGGGGGGTGG AGAGTGAGGG GAGGGAACTT AGAGGACAGG

1701 TCAATAGGGG CAGCAAACCA CCATGGCACA CATATACCTA TGTAACAAAC

1751 CTGCACGTTC TGCACATGTA TCCCTTTTTT TTAGAAGAAG AAATAATGAA

1801 AAAAAACCTT TTTTCTATTT ATATAATCAT GGCATTTATA AGCATCTCTA

1851 TAGAGAAGGA TAATTGTGCT GAGATTAGAC AGCTGTCTGA GCACCTCACA

1901 CTGACCTATT TTTAACAAAA TGACTTTCCA CATCACCTGA TTTCGGCTCC

1951 ATGCRGGGTA AGCAGTTCCT AAGCCCTAGA AAGTGCCGAT CATCCCTCAT

2001 TCTTGAATTC CTCCTTTTAT TTACCAAAAT TCCTGAGCAT GTTCAGGAAA

2051 GATGAAAAGC TTATTATCAA AATAAGTGGC TGAGATAGAC TTCTTGTCAC

2101 ATTTGTTACA GTAAAATGGG TCTCCAAGAA AGAAAGATTT GCCTTGGGCT

2151 CTAGCATGGC CATTTATTTA AGAAAGCATC TGAAACATGA AGCTACCACA

2201 GCATCTCTCC TGTGGTTCCA GACGGAAGCC TGAGAGTCTA GGAGGAGGTG

2251 GACCGAGAAA CCCTGCCAAA GTAACTAGTA GTGCCGGGTT TCTCACAACA

2301 CGATGCAAAG GGGCTAGAAT CAGATGACTA TTTTCATGTT TCAACATACT

FIG. 1 Cont.

2351 ACACACTGGA AAACGTTACG GCAGACTCTA CTTTATAATG GGGCTGCAAA

2401 TGTAAAATGA CTACTAGAAC TAGGTCCTCT TAATAGCAGC AAAGTTTAAA

2451 AGGGTCAGAG GGAGCTCCAG ACACAGGTTA GATTTGATTT CTCTCCTAGT

2501 TCTGCTGTGA ACAAGAGGTA TAAGTTTGGC CAACTCACTT AACCCCTGAA

2551 GCTCAGTTAC CTTATCTGTA AAATGATTGC ATTGTACTAG GTGTTCTCTA

2601 AAATTTCTTC TACCTCTGAC TTTTTAGGAG ACTAATTTTT AACTCCTTTT

2651 TAAGCTATTG GGAGAAAAAT TTAATTTTTT TTCAAAAGTT ACCTTGAATC

2701 TCTAGAGCAG TTCTCAAAAC TATTTTGTCC CAGGCAAAGG AAATGAGACT

2751 AGGTACCCAG AATGAGGCAC CCTGCATAAA GCTCTGTGCT CTGAAAACCA

2801 ATGTCAGGGA CCCTGTGATA AATAATTAAA CCAAGTATCC TGGGACACTG

2851 CTAGTGACAT CGCCTCTGCT GATCACTCTT GCCAGCGAGA CACTCTATAC

2901 TTGCTTTCTC ATCATTGGCA TCCAAACTGC CTACTAATCC ATTGCTTTGG

2951 AAAGTTTTTT TTAATAAAAA GATTATTTCT ATTAGGAGGA AAACATCCCA

3001 TGTTAAATAG GAAAATTAAC TGAAATCATT TTCAGATGTG ATTTTTAGCA

3051 CTTATAGCCA TTTCAAACCA TGGTATTCAT TTATACTATG CTATTTATTG

3101 TAAAACTTCT TTTTTTTTCC AAGGAAAATA AGATAGTTTG CTTTATTTTA

3151 AAACAGTAAC TTTCTTATAT TGGGGCACTG ACCAAAATTC AATACTGGTA

3201 CAAATATGTT ACCTAGGGGG TCAAAATATG TGCCAGGTGA ATTTTCTGAA

3251 TTTCTCTAAA GAGAGAATTT TAAACCTTAT AAAACAATTA GAAACAAGTG

3301 AGTGAGAGGT GAGCATCAAC AACCTGTGTA ACATAAGCCA CAGTACAAAT

3351 TTAAGCTGAA TAACCAAGCC ATGTCAGTTA TCCCAAATCA TTTTTGTTAA

3401 TATTTAGGAG GATACACATA TTTTCAATAA CTTAAAAGTG AATCTTTACT

3451 CCTATCTCTT AATACTCGAA GAAGTATAAC TTTCTTCTTT TACTAGATTT

3501 AAATAATCCA AATATCTACT CAAGGTAGGA TGCTGTCATT AACTATAGCT

FIG. 1 Cont.

3551 GAGTTTATCC AAAATAGAAA AATCATGAAG ATTTATAAAG CATTTTAAAA

3601 ATAATCATTT ATAGCAAGTC CTTGAAAGCT CTAAATAAGA AAGGCAGTTC

3651 TCTACTTTCT AATAACACCT ATGGTTTATA TTACATAATA TAATTCAACA

3701 AAACAGCATT CTGACCAATG ATAATTTATA GGAAATTCAT TTGCCAAGTA

3751 TATGTTTTAT TATAAAGTTA ATATTTTGAC CAATCTTAAA AATTTTTAAA

3801 CTCTATTCTG ACATTTCCAG AAGTATTATC TTAGCAAGTC ATCTTTATGA

3851 TACCACTTAT TAAACTGAAG AGAAACAAGA TGGTACATTC TGGGTTTTAC

3901 TTTAAAAGGG ATTTGATTCA ATAATTTGAT TTATCACTAC TTGAAAATTA

3951 CATTTTCTTC CTCAGACTGG ATGGCAATGA GATGAAAGCA GCTTTCCTGG

4001 CTCTCAACTT CCCTTCTTCA TCAATTTTTC CAGCGTTTCA TAAGGCCTAC

4051 ACTAAAAATT CTAAAACTAT ATATCACATT AATATAATTA CTTATAATTA

4101 ATCAGCAATT TCACATTATC GTTAAAACCT TTATGGTTAA AAAATGCAAG

4151 GTAAGAGAAG AAAAAAACAC ATTGAACTAG AACTGAACAC ATTGGTAAAA

4201 TTAGTGAATA CTTTTCATAA GCTTGGATAG AGGAAGAAAG AAGACATCAT

4251 TTTGCCATGT AACAGGAGAC CAATGTTATT TGTGATTTCA GATTGTCTTT

4301 GCTGGACTTC TTGGAGTCTT TCTAGCTCCT GCCCTAGCTA ACTATGTAAG

4351 TCTCACCTTT TCAAGTTTGC TACCAAAATG CATTTGCAAG GAAATGTGAT

4401 ATTAAATCAC TCTCAATCTC TTATAAACTT CAGAATATCA ACGTCAATGA

4451 TGACAACAAC AATGCTGGAA GTGGGCAGCA GTCAGTGAGT GTCAACAATG

4501 AACACAATGT GGCCAATGTT GACAATAACA ACGGATGGGA CTCCTGGAAT

4551 TCCATCTGGG ATTATGGAAA TGTAGGTAGT CAACGTGCAA TTTTCACTTT

4601 ATTGTTTAAA AATACGACTT CTTTTTAACA AAAAATGTGC ATGTTAACCA

4651 TAAAGAAATT AAAAATAAAT TCTAATTACA CATAGCATAC AGTTATAAGT

FIG. 1 Cont.

4701 AAAGGTGACC ATTTTGCTCA TCCGATTTTG TTCCCTAGAG ATAACTACTG

4751 TTAATAAGTG TTGCATGATC AGTTAAAATT CAAACCAACA AACACTATGT

4801 TCAAGGGATT GTGGGTATAT ACAACAAATA TGAACATCCT TTTGCCTTGC

4851 CTGCAGATAC CCTCAATAAT GCTGAAAGAC TTATACAACA TTACTGCTTC

4901 CAAAGCTTAG ACTATCTCAC TTTGTTTTCA AAGGAGGTTT TACGACCTTC

4951 TAAAGAGATT GAAATTGACA TTTCACCTAA AACTCGGGAA ATGTAAATGA

5001 CAATATTAAT TGGTAAGAGA GGAAAGAAGA AAGAAAGAAG GAAGGAAAGA

5051 AAGAAAGAAG GAAGGAAGGA AAGAAAGAAA GAAAGAAAGA AAGAGAGAGA

5101 AAGAAAGAAA AAGAAAAAAG AGAGAAAGAG AGAAGGAAAG AAAGAGAGAA

5151 GGAAAGGAAA AGAGAAGCAA AGAAAGAGAG GAGCAAAGAA AGGAACACTT

5201 AGCACTAGTT GGGAGACCCA ACTCTGGAAT TATCAGCTAT ATATTTAACA

5251 AACGTTATAC TTTTAAATAG CAAACTCTTT ATTGTTTCAA TTTTATCTGG

5301 TCAATTGGAA AAATAATTTT TGTCTTATCT GTCTCCTTGA AATGTGAGGA

5351 TCAAAGGAGA CTAAAACATG ATAGCTTTTA AAGTCTATTT CAGTAAAACA

5401 GACTTATATA GAGGGGTTTT TATCATGCTG GAACCTGGAA ATAAAGCAAA

5451 CCAGTTAGAT GCTCAGTCTC TGCCCTCACA GAATTGCAGT CTGTCCCCAC

5501 AAATGTCAGC AATAGATATG ATTGCCAAGC AGTGCCCCAT CCAGTGCTCT

5551 TATCCCAGCT CATCACGATC TTGGAGTTCC CATTTCTCTC TGCAGGTGGA

5601 ACTGACCTCT GATAAGAAAA GCTCCTCGGA GAACACATGC CTCACTATTT

5651 GCCATCTACT TTAACAGGGC TTTGCTGCAA CCAGACTCTT TCAAAAGAAG

5701 ACATGCATTG TGCACAAAAT GAACAAGGAA GTCATGCCCT CCATTCAATC

5751 CCTTGATGCA CTGGTCAAGG AAAAGAAGGT AAAAATAAAA GGCTTTTTAT

5801 TTTTGGTGAG GGGAGAGGTT TTACATCCTT CAGTAAATAA CGAGAAGATC

5851 ACAGTCATTC CCTCTTGACT ACAGTATGTT GTAGTGTGCA GCACAAAGGG

FIG. 1 Cont.

5901 GGAAGTTATT GGTGATTGCC TGAGGGAAGG CAACTTCTGC CACATCAAAT

5951 GCTGTGGCTC ACACCTACCT CTACAACCGC TGAGCAAAGC ACTTGAAACC

6001 TTGACTGTTA GAGGAGCAAA GCTCTGGTCA CACCAATAGG AGCCTCAGTA

6051 CTTTGCCAAG GACATTTTTC TGCAAGAGTT AGTTAGGGTT ATTAGATTTA

6101 GCAAATGAAA ATAGAAGATA TCCAGTTAGG TTTGAATTTT AGGTAAGCAG

6151 CAGGTCTTTT TAGTATAATA TATCCTATGC AATATTTGGG ATATACTAAA

6201 AAAAGATCCA TTGTTATCTG AAATTCAAAT GTAACTGGGT ATTGTATATT

6251 TTGTCTGGCC ATACTAATCC AGGTGAGTGG AAAGAAGAGA TCCATAATGT

6301 TTTAAAATAT TTGCCTGAGT TCATATTCCT ATAACTGATA AATGAGTACC

6351 TTTCATTGAC AAGGTAGAGA AAATAAATAA ACTGCATTCT CAGAAGATGA

6401 TTATTACATA GTCTAATCCA AGGAATCTAT GATGACCAAA TGAGGTCCAA

6451 GTTGCAGAAT AAATTAAGCC TCAGACTTCT GTGTTTATGA GAAGCTGAGG

6501 TTTCAAACCA GGTAAATCCC TTAGGACACT TAGAAATGCT AAGATATACA

6551 GAATAAGCTA GAAATGGCTC TTCTTCATCT TGATTATGGA AAAATTTAGC

6601 TGAGCAACAC TCACTGTTGG CCTCGTATAC CCCTCAAGTC AACAAACCAC

6651 TGGGCTTGGC ATTCATTCTC TCCCATTCTT CCTTTCTACC TCTCTTTTCC

6701 ACACTCAGCT TCAGGGTAAG GGACCAGGAG GACCACCTCC CAAGGGCCTG

6751 ATGTACTCAG TCAACCCAAA CAAAGTCGAT GACCTGAGCA AGTTCGGAAA

6801 AAACATTGCA AACATGTGTC GTGGGATTCC AACATACATG GCTGAGGAGA

6851 TGCAAGGTGA GTAGCATCCC TACTGTGCAC CCCAAGTTAG TGCTGGTGGG

6901 ATTGTCAGAC TATCCTCGCG CGTGTCCATA GTGGGCACCA GTGATGCAGG

6951 GATGGTCATC AAGGCCAACA TTTGTGCAGT GCTTGCTCTG TGCCAGGTAC

7001 TGTTCTATGT GCTTTAAGTG TGTTAACTCG GTTCTTCACA GCAATCTTAT

7051 AGGTTCTATT TTAATCCTAC TTTATGGATG AGGAAACTGA GGTACAGAGA

FIG. 1 Cont.

7101 GGTCACAAAA TCCTTGCCTG GGTCAATTCC AAGCATTTTG GCTGTGGATT

7151 CTGTGCTCTT AAATATTATG GAACACTGCC TTTTAAGTGT GAATCAAGAG

7201 TAGACTCAAG TCATATTCAA AAGAATGCAT GAATGGCTAA ATGAAAGAAG

7251 AATGCTAATA GAATCTATTA ACTTTCTATA GCTCAGACAA TCACTTAATT

7301 TCTGGACATT CAAAGAACAG CTGCACACAA ACAAAGTGTC TACCTAGGGA

7351 CCTAACTTAA TGGCAATTTT CCAGATCTCT GAATTGATTG ATTTCATCAC

7401 AACAAGTAGA TAAACCTTGA CATTAGCACA TAGCTAGTTT GGAAACCCCT

7451 ACTCCCCCAA TCCCCTCCAA GAAAAGAGTC CTTAAATAGA CATTAATATA

7501 GGCTTCTTCT TTTCTCTTTA TTAGAGGCAA GCCTGTTTTT TTACTCAGGA

7551 ACGTGCTACA CGACCAGTGT ACTATGGATT GTGGACATTT CCTTCTGTGG

7601 AGACACGGTG GAGAACTAAA CAATTTTTTA AAGCCACTAT GGATTTAGTC

7651 ATCTGAATAT GCTGTGCAGA AAAAATATGG GCTCCAGTGG TTTTTACCAT

7701 GTCATTCTGA AATTTTTCTC TACTAGTTAT GTTTGATTTC TTTAAGTTTC

7751 AATAAAATCA TTTAGCATTG AATTCAGTGT ATACTCACAT TTCTTACAAT

7801 TTCTTATGAC TTGGAATGCA CAGGATCAAA AATGCAATGT GGTGGTGGCA

7851 AGTTGTTGAA GTGCATTAGA CTCAACTGCT AGCCTATATT CAAGACCTGT

7901 CTCCTGTAAA GAACCCCTTC AGGTGCTTCA GACACCACTA ACCACAACCC

7951 TGGGAATGGT TCCAATACTC TCCTACTCCT CTGTCCACTG CTTAA

FIG. 1 Cont.

```
1   CATGCTTGCC TACTCCTCTG TCCACTGCTT TCGTGAAGAC AAGATGAAGT
51  TCACAATTGT CTTTGCTGGA CTTCTTGGAG TCTTTCTAGC TCCTGCCCTA
101 GCTAACTATA ATATCAACGT CAATGATGAC AACAACAATG CTGGAAGTGG
151 GCAGCAGTCA GTGAGTGTCA ACAATGAACA CAATGTGGCC AATGTTGACA
201 ATAACAACGG ATGGGACTCC TGGAATTCCA TCTGGGATTA TGGAAATGGC
251 TTTGCTGCAA CCAGACTCTT TCAAAAGAAG ACATGCATTG TGCACAAAAT
301 GAACAAGGAA GTCATGCCCT CCATTCAATC CCTTGATGCA CTGGTCAAGG
351 AAAAGAAGCT TCAGGGTAAG GGACCAGGAG GACCACCTCC CAAGGGCCTG
401 ATGTACTCAG TCAACCCAAA CAAAGTCGAT GACCTGAGCA AGTTCGGAAA
451 AAACATTGCA AACATGTGTC GTGGGATTCC AACATACATG GCTGAGGAGA
501 TGCAAGAGGC AAGCCTGTTT TTTTACTCAG GAACGTGCTA CACGACCAGT
551 GTACTATGGA TTGTGGACAT TTCCTTCTGT GGAGACACGG TGGAGAACTA
601 AACAATTTTT TAAAGCCACT ATGGATTTAG TCATCTGAAT ATGCTGTGCA
651 GAAAAAATAT GGGCTCCAGT GGTTTTTACC ATGTCATTCT GAAATTTTTC
701 TCTACTAGTT ATGTTTGATT TCTTTAAGTT TCAATAAAAT CATTTAGCAT
751 TG
```

FIG. 2

1 MKFTIVFAGLLGVFLAPALANYNINVNDDNNNAGSGQQSVSVNNEHNVAN 50

51 VDNNNGWDSWNSIWDYGNGFAATRLFQKKTCIVHKMNKEVMPSIQSLDAL 100

101 VKEKKLQGKGPGGPPPKGLMYSVNPNKVDDLSKFGKNIANMCRGIPTYMA 150

151 EEMQEASLFFYSGTCYTTSVLWIVDISFCGDTVEN 185

FIG. 3

```
1    GAATTCAAAC AGCAGGCCAT CTTTCACCAG CACTATCCGA ATCTAGCCAT
51   ACCAGCATTC TAGAAGAGAT GCAGGCAGTG AGCTAAGCAT CAGACCCCTG
101  CAGCCCTGTA AGCTCCAGAC CATGGAGAAG AGGAAGGTTG TGGGTTCAAG
151  GAGCTTTTCA GAGTGGAAAT CTGTGGATCA GTGATTTATA AAACACAGTT
201  TCCCCCTTTA TTAGATTTGA ACCACCAGCT TCAGTTGTAG AAGAGAACAG
251  GTTAAAAAAT AATAAGTGTC AGTCAGTTCT CCTTCAAAAC TATTTTAAAC
301  GTTTACTTAT TTTGCCAAGT GACAGTCTCT GCTTCCTCTC CTAGGAGAAG
351  TCTTCCCTTA TTTTAATATA ATATTTGAAA GTTTTCATTA TCTAGAGCAG
401  TGGTTCTCAT CCTGTGGGCC ATGAGCCCTT TGGGGGGGTT GAACGACCCT
451  TTCACAGGGG TCACATATCA GATATCCTGC ATCTTAGCTA TTTACATTAT
501  GATTCATAAC AGTAGCAAAA TTAGTTAGGA AGTAGGAACA AAATAACGTT
551  ATGGTTGTGG TCACCACTAT GTTAGAGGGT CCGCAGCATT CAGAGGGTTG
601  AGAACTGTTG TTCTAGAGGC AAATAAGAAG ACAGAGTTCC TTGATAGGGC
651  CCAGAGGCAG TGAAAGAAGT TTCCACGTAG AAAGTGAAGA AGGTCTGGTG
701  TCCGAAGCAG TGAGGAACTT AAAAAAAGAA AACCAAAAAC ATTGCCAACT
751  AACAGTCCAG GAGAAGAGCG GGGCATGAAA GGCTGAGTTC CCATGGGATG
801  CCTTGAATGG AATCAGAGTG TGGGAAAATT GGTGTGGCTG GAAGGCAGGT
851  GCCGGGCATC TCAGACGCTG GTAGCTGGGG AAACAGGAAA CCCCTTTAGG
901  ATCCCAAGAT GCCATTCCAA TGAGCTTGAG ATTTTTCTCA TGGACTGCCA
951  GTGAATGTTT CTACGCTCCG GAAATTAATG TTTACTTATT TTCCATATTC
1001 TAGGGGAGAA CCCTGGGAAA AATGGAGGAC ATTCATTGAA ATATCTGAGT
1051 CCTGGGATAA GGCAGGCTTG GTCCTACAAC TCTGGTAAAA GTCCATCAGG
1101 AAGTGCCTTG ACCAAGGCTG GAGTGGAGAG CTGTTGGTGA GATGTAAGGG
```

FIG. 4

1151 CAAGGTTTAG TTGCTAGATA TGTAGATGGC AAGATGGTGC TGCCAACAGC

1201 CCCCAGAGCT CTAACCCACT GAGAAACCCA GGAATGAATG ATGGGAGATG

1251 GCTTTGGTGC CAGCTGCTAG TGACATGGCT GGAAAGCTGC ACTGGCTTCG

1301 AGGCCAGACA ATTCCTCAAG GAAACATCTG GCCAGGGTGC AAGGGCCAGT

1351 TTCCTTCCTT GGAGTTCCTT TCACAGCTAA GAACATCATC CCCCAACCAC

1401 TGGTTTTGTT AAAAAGTTTT CAGTATGACT TGAGCATGGT CAAGAAGCAT

1451 AGAGAGGGGG AAATAAGGGT GGAAGGAGCT GGAGAAAGCT TACAATAGGA

1501 CTGGGTAAAG GGAAGGAGAA GAAACCATTC CCGCATTCCC ATAGGAGCCA

1551 GTACCAGGAA GGGCAGGTGT ACACACAGAT CTCATCTAAG GCCATGTTTG

1601 GTTTAGGGAT TACTCTTCTC CCGAATCTGA GCAGCAGCAA TACGTAAAAT

1651 ACCCACACCC ATGGCTTCCA TATTCCAGAA CTTATCACAA ACCGTGTAGA

1701 GTTTACTGAG ATACCTTCGT CAGAGGATGA GTCAGAGGCC TCCTGCCTAA

1751 GGGCCCTACT GAGCAGGCAG CTAAAGGCTT CCGGGCCTCT GCAGCTCCAC

1801 AGATACAGGA GAGGGAAGCA GATAAGCCGT GGACTCCACC TGAGCACACC

1851 TAGCTTGAGC AAAGCTGGTC AGGTACAAAT AGCAGAGGGC TGAATGTCTG

1901 TGAGCACGCC GCCTGATCCT CTGCTCCACC ACACTCCTGC CGCCATGAAG

1951 CTCACAGTAA GTCAGATCTT CTTTTCAATG CAGCACCATA CAACATTAAT

2001 AGTCAGGGGT GAGGGGGTCT GACTCTTACG GCACTGTTAC CATAGTGGAA

2051 ATATTCTCCT TTCTTTTCAT GGAATCATGG TGTTTACAAG CATGTCCATA

2101 GAGAAGAAGA ATTGCCCCGG AAGAGCCTGT CACAGGCTGA ATACTGTAGA

2151 ATTGTCTTTC ACACCATCTG TTCCAAGGTT CTACTTAAGA CGAGCAGTCT

2201 CTGGGCTCCA GAAAGAGTCT TTCTTAGCCT TGATCTCTTT CTTATTTCTG

2251 ATTTCTCCTT TCTTATCCAT GATTTCCACT TTTACCAGTT CTGGGCATGT

FIG. 4 Cont

2301 TCCGGTCAGA CTGGAAGATC ACTGTTGTCA AAACTAGTCT TCAACACTCT

2351 TGGCTGTTAA CATGAAAACA ACGGTCCTTG GGCCCTGTGC AAGCATTTCT

2401 TGGAGAAAGT CTCTGGGGAT GAAGCTATCT CAGTTTCCCC ACTGAAGTCC

2451 TAGGATACAG AGGCTCAAAC AGAGTGCACA TATTCAATTT CAGCATACTC

2501 TATTGGCGCT GCTTTATGAA TCATATGAAT TTATGGAATT GGAAATGTAA

2551 ACTATGACCA AGAAGCGTCC ACCTCAGAAC AGGTTGGGTG GGGAACTCCA

2601 AGCACAGGCC AGAGGGCTGC GTTTCTCTTC TAGTTCTGTC TAGAGGAGTG

2651 GTTCTCGACC TTCCTAATGC TGTGACCCTT TAATACAGTT CCTCACGTTG

2701 TCGTGACTCC CAGCCATAAA ATTACTTTCA TTGCTACTGC ATAACTGTAA

2751 TTTTGCTACC ATTATGAGTT GTAATGTAAA TATCTGATAT GCAAGATACC

2801 AGATAACCTA AGAAACGGTT GTTTGACCTT TAAAGGGGTC ACAACCCACA

2851 GGTGGAGAAC TACTGGTCTA GGGTCCTTTA CAGTCCTTTA GCTGCCTCAT

2901 TTACAGGAGA TAACATCATG CTCAAAAACT CCCTCCACAT TTGGCTTTTT

2951 GGGTTGTTTT GTTTTGTTTT TCAAGACAGG GTTTCTCTGT GTAGCCCTGG

3001 CTGTCCTGGA ACTCACCTTT GTAGACCAGG CTGGCCTCGA ACTCAGAAAT

3051 CCGCCTGCTT CTGCCTCCTG AGCGCTGGGA TTAAAGGCGT GCGCCACCAT

3101 GTCTGGCTCA CATCTGGCTT TTTAAGAGAC CGATTTTAAC TTCTTGCATT

3151 GAAAATAAAT ATAGTAGAAA TGCTTAACCT ACTAAGACAA TAAAAACAGG

3201 ATTCCTTCTG CTAGGAAGAA CACGTTCCAG ACTAAGGAAA AAAACCTTTT

3251 CAGGGCTTTC ATTACACTGT GCCATGCACT AATTTTATGT TTTCTTCATC

3301 AGTTTTCAGT GTCTGAAATT CAGTGTCAAA ATTCTAAGAC TACATATGAA

FIG. 4 Cont.

3351 TATCATTACA GTAACTCAGC AATTCTATGT TACCAGTAAG TTTTTCTGTA

3401 GTTTAAAAAA AAGGTGGAAG AAGAAAGCAC AGATAGTTTA GCACATGGGT

3451 AAAATCAGTA ACTATTTCTG ATGAGCTTGG TGAAGATGCT GTAAACCATG

3501 CGACCACCAG TCCTGTTCTC TGTGCTTTCA GATGTTCGTC GTGGGTCTGC

3551 TTGGCCTCCT TGCAGCTCCT GGTTTTGCTT ACGTAAGTCT CATTTTTCTG

3601 AAGTTCATTG TCAAAACTGC ATTTACAGTG AAATGTGATC TTAAGTCACC

3651 CTCTGCTTCT TATGAACATT AGACGGTCAA CATCAATGGT AATGATGGCA

3701 ATGTAGACGG AAGTGGACAG CATTCGGTGA GCATCAATGG TGTGCACAAC

3751 GTGGCCAATA TCGACAACAA TAACGGCTGG GACTCCTGGA ATAGCCTCTG

3801 GGACTATGAA AACGTATGTA ATGGACACAC AGGGTAAAGA TATGGTGTAG

3851 CCACCACCCA TTAAAATTTC TGAGGTGAAT TCTAGCTGTT CATGAACATT

3901 AAAAGCTACC AGTAAAAGTG CCCATTCCAC TCAAAACAAT TTTACTTTTT

3951 TGCATATAAT TATTGCTAAT AAGTATTACA CAATAGGTCG AAATTCAAAG

4001 GGATCAATAG TAAGGATAAA AACTATGTAC AAAGACAAAC ACAGCATCCT

4051 TTGGTCTTCC CTGCAGAGAG TCTCCATGAT GTTAAAGGTC CAATGTTTTA

4101 TGGAGGCTGA ATGAAATACG AATGCCTCTG TGATGGAAAA GGCCCAACAT

4151 CTTATGGAGA ATGAGTGAAG TATGAATGCT ATTAGTTGTA AGAGAAGGCG

4201 ATGCAAAGCA ACACTTGGCA CCACCTGCCA ATTACTACTT TCCTATTTAA

4251 ATGTAGTTTA AAAAGCAAAG CCTGTCTTCC CTGCCTCCTG GAAACACTGC

4301 GGATGGAGGT AGACCAAGGT ATGACAGCCT TTAAAAGTTT GTCAGCAAAA

4351 CACTCCCCCA TACACACATA CACACACCCT CCTACTACAC TGGAACTGAA

FIG. 4 Cont

4401 GCAAAGGCAG TGGGTTAGAT ATATCCACCC TCTAAGAGTT TGCAGGTCAT

4451 CTATATATGA TAGCCAGAGA CACAACTGCA GGACAGCCAG ACTCTGAGCA

4501 CTCTCCCCAG CTCCTTGTAG CTCTGTTTCA GTGGTGACTT GTGACAAGAA

4551 TCCTGGGGAA CCTGTGCCTC ACTGTTCTCT GTCTTCTTTA ATAGAGTTTC

4601 GCTGCCACGA GACTCTTCTC CAAGAAGTCA TGCATTGTGC ACAGAATGAA

4651 CAAGGATGCC ATGCCCTCCC TTCAGGACCT CGATACAATG GTCAAGGAAC

4701 AGAAGGTAAA GTCCTGCCTT CTTCTTTGGA GTGACAGGAA GTCTTACAGT

4751 CTCCAGTACA CAGTGAAGTC ACCCCCATTC CCTCTTTGGT GGAGCATGAC

4801 AGCATGTTTG TCATGATAAA TGCCACAAAC ATGTAAAACT GTTCAGTGTC

4851 TGCCTGAATG GAGGGTGGCT TCCACTGTGT CAGATGCCGT GGCCCACATC

4901 TGCCTCTGCA GGGTCCAGTA AAGCACTGGC TATCTTGAGT GTCAGAGACC

4951 CAAAGGTCTG TACACTTCAG TACAAGCCCT CCATATTTCA AGGGCACACT

5001 CCTACAGTCG TTGGGGTTAT CAGAACTAGC AAACATAGAG ACTGGATTTT

5051 CAGATGAAAA GAAATCCTTT TTAAAGTCTA AGTATGCCTT ATACAATGTT

5101 TGAGATATTC TCAATACTAA AAAAAAAAAA ATTGTTGCTT GCTTGAAAAT

5151 CAAATGTAAC CAAGTGTCCT ATATCCAGTG TCAATCATGG CTGTAGTAGA

5201 TGGGAAGAGG GAGCCCGTGG TTTTCACAGT CAGACGCCTG AGTTATTCTT

5251 CTAAGTGATA AATTGGTTCC TATAACAAGC AAGCCAGTGA ATATAAATAA

5301 GCTCTATCTC AGAAGTTATC CTGTAGTGCT ACCCTAGAAT CTAAGAGAGC

5351 AAAAGTGCTT CAAATTTCAG AATAAGTTTT GCTTTGGACT TCTGTTTTTC

5401 TAAACAACTA TAACTTCAAA CCATCTAAGC CTCGTGGGAC ACTTAGAAAT

5451 ACCAAGCCAT TCAAAGCTAG AATTGTTTCT TCACCTTACT TGAAAACAAA

FIG. 4 Cont.

5501 ATGACAACCA AAAATTGTCC CCACTGCCCT TGTACATCTT CAGATCAGTA

5551 AAGTCCTGGG CTCAGGGATC ATTCACTTTC TTTCTTTCCT TTCACACTCA

5601 ACTTCAGGGT AAAGGGCCTG GAGGAGCTCC TCCCAAGGAC TTGATGTACT

5651 CCGTCAACCC TACCAGAGTG GAGGACCTGA ATACATTCGG ACCAAAGATT

5701 GCTGGCATGT GCAGGGGCAT CCCTACCTAT GTGGCCGAGG AGATTCCAGG

5751 TGTGTACCCT GAGATGCTGT ATATCCCAAT GCAGTACTGA GAGAGCCATC

5801 AGACACTCTA AAGTGTGACC ACAGACGGAC CAATCATGTG GATTATCAGA

5851 GCAAACACTT GCTTGCTCCT TGTCAGACAG TTGTCCATGC TTCAAAAGTT

5901 CATTAAAAAA AATAGTTCAC AGGCTCCTCA CAGAAACCTT AGTAGAATCC

5951 ACAGCTTCTG CTCTTAGTCT TACTTTTTAG AAACTGAGAC CCAGAGAAAG

6001 GTCACAAAAC TTTTGTCTGG CTCAGGTTCT ATGTCTTTAA CTTTATAGAA

6051 TACCGTCTTT CTGGGTGGGT GGGCTCTAGA GTAAACTTCA AGTGAGTTCA

6101 AGGAAAGCAT GAGAAGTAGG GAAGACCAAA TGAAAGGAGA ATGCCAATGA

6151 AATCTATCGA TTCTATAGCG CCAATGCTTA ACTCCTAGGC GTTCAAAGAA

6201 TAGTATCCAC AAGGTGTCAG CCTAAGATCC TAATCTAACA GCAAGTTTTC

6251 AGATCTCTGA AGTGAAAAGA GAAAGCAAGA GAGGAACAGA GACAGAAACA

6301 GTAAGAGACA GAGAGGCAGA GACAAAGAGA CAGGGAGAAT AGAGAGGGAT

6351 TAAAATTAAT ATATAGTTTA GAAATTACGA CTCCTCACAG TCCCTGCAGA

6401 GTCCTAGGAT AGGCACTGAT TTGGACTTCT TTTCTTCTCA CTAGGACCAA

6451 ACCAGCCTTT GTACTCAAAG AAGTGCTACA CAGCTGACAT ACTCTGGATT

6501 CTGCGGATGT CCTTCTGTGG AACATCAGTG GAGACATACT AGAAGTCACA

6551 GGAAAACAAC CCGTGGGCTC TGACCATCGC AATGCTTGAT TATGAGAGTG

FIG. 4 Cont.

6601 TTCTCTGGGG GTTGTGATTA GCTTCTTTAA GGCTCAATAA ACCCACGTGG

6651 CAGCACATCC AGTTTGTAAT GACATGCCTC ATGACTTCTA TGGGAGTCCA

6701 ATGTGGCACC TGCCAGCCTG TATTCAGGAC CTCTCCGCTA TAAAGCATCC

6751 CTCCAGAGTT TTCAAATACT ACAAAGCACA GCCTGGGTTT GGGCTCAGAT

6801 AGGCCACTGC TGCCTGACTA CATTACAGAC AAACAAGTTT TAAAAGAAAG

6851 AAAAAAGAGC TCAGAGTGGC TGGAATCAGC AAGGGTGTTT TTCCTGCAAG

6901 GAGCCAGAAG TATCAATAAT CACCCAAGGA GGAGACACTG GGAATGAGAG

6951 ACTAGAACAC ACGCCTGCAG ATACGGAGAA CCTCAGCATT GCCGCTCTCT

7001 CCCATAACTG CACACCCCCT TCTGTAAACT CTGCTTCTTT CTTTCACCTG

7051 AAGATGGCCC TTGCTTTTTT TTATTATAGG ACANGATAAC TAGACCAGAA

7101 AGTCAACCTG ACTCTCTACA TTTATATGTC TTCCCAGNTC AAGAAATATT

7151 ATTTACTGGT GAATGGCACT TCTATATTCC CTTGGTTCAA TAAGTCTACA

7201 GGATCCATTC ATTGACAGGC CAAGAGTGAG ATCACATGAT ACCCAAGCAC

7251 ATGGGTCTTT CCTTGAAGGA GAAGGATCCA

FIG. 4 Cont.

1 ATGTTCGTCGTGGGTCTGCTTGGCCTCCTTGCAGCTCCTGGTTTTGCTTACACGGTCAAC

61 ATCAATGGTAATGATGGCAATGTAGACGGAAGTGGACAGCATTCGGTGAGCATCAATGGT

121 GTGCACAACGTGGCCAATATCGACAACAATAACGGCTGGGACTCCTGGAATAGCCTCTGG

181 GACTATGAAAACAGTTTCGCTGCCACGAGACTCTTCTCCAAGAAGTCATGCATTGTGCAC

241 AGAATGAACAAGGATGCCATGCCCTCCCTTCAGGACCTCGATACAATGGTCAAGGAACAG

301 AAGGGTAAAGGGCCTGGAGGAGCTCCTCCCAAGGACTTGATGTACTCCGTCAACCCTACC

361 AGAGTGGAGGACCTGAATACATTCGGACCAAAGATTGCTGGCATGTGCAGGGGCATCCCT

441 ACCTATGTGGCCGAGGAGATTCCAGGACCAAACCAGCCTTTGTACTCAAAGAAGTGCTAC

501 ACAGCTGACATACTCTGGATTCTGCGGATGTCCTTTTGTGGAACATCAGTGGAGACATAC

561 TAG

FIG. 5

```
1   MKLTHFVVGL LGLLAAPGFA YTVNINGNDG NVDGSGQQSV SINGVHNVAN

51  IDNNNGWDSW NSLWDYENSF AATRLFSKKS CIVHRMNKDA NPSLQDLDTM

101 VKEQKGKGPG GAPPKDLMYS VNPTRVEDLN TFGPKIAGMC RGIPTYVAEE

151 IPGPNQPLYS KKCYTADILW ILRMSFCGTS VETY
```

FIG. 6

1 atgcctgact tctcacttca ttgcattggt gaagccaaga tgaagttcac 51 aattgccttt gctggacttc ttggtgtctt cctgactcct gcccttgctg 101 actatagtat cagtgtcaac gacgacggca acagtggtgg aagtgggcag 151 cagtcagtga gtgtcaacaa tgaacacaac gtggccaacg ttgacaataa 201 caatggatgg aactcctgga atgccctctg ggactataga actggctttg 251 ctgtaaccag actcttcgag aagaagtcat gcattgtgca caaaatgaag 301 aaggaagcca tgccctccct tcaagccctt gatgcgctgg tcaaggaaaa 351 gaagcttcag ggtaagggcc caggggggacc acctcccaag agcctgaggt 401 actcagtcaa ccccaacaga gtcgacaacc tggacaagtt tggaaaatcc 451 atcgttgcca tgtgcaaggg gattccaaca tacatggctg aagagattca 501 aggagcaaac ctgatttcgt actcagaaaa gtgcatcagt gccaatatac 551 tctggattct taacatttcc ttctgtggag gaatagcgga gaactaa

FIG. 7

1 MKFTIAFAGL LGVFLTPALA DYSISVNDDG NSGGSGQQSV SVNNEHNVAN

51 VDNMNGWNSW NALWDYRTGF AVTRLFEKKS CIVHKMKKEA MPSLQALDAL

101 VKEKKLQGKG PGGPPPKSLR YSVNPNRVDN LDKFGKSIVA MCKGIPTYMA

151 EEIQGANLIS YSEKCISANI LWILNISFCG GIAEN

FIG. 9

| | | | |
|---|---|---|---|
| Human | 1 | MKFTIVFAGLLGVFLAPALANYNINVNDDNNNAGSGQQSVSVNNEHNVAN | 50 |
| Pig | 1 | MKFTIAFAGLLGVFLTPALADYSISVNDDGNSGGSGQQSVSVNNEHNVAN | 50 |
| | 51 | VDNNNGWDSWNSIWDYGNGFAATRLFQKKTCIVHKMNKEVMPSIQSLDAL | 100 |
| | 51 | VDNNNGWNSWNALWSYRTGFAVTRLFRKKSCIVHKMKKEAMPSLQALDAL | 100 |
| | 101 | VKEKKLQGKGPGGPPPKGLMYSVNPNKVDDLSKFGKNIANMCRGIPTYMA | 150 |
| | 101 | VKEKKLQGKGPGGPPPKSLRYSVNPNRVDNLDKFGKSIVAMCKGIPTYMA | 150 |
| | 151 | EEMQEASLFFYSGTCYTTSVLWIVDISFCGDTVEN 185 | |
| | 151 | EEIQGANLISYSEKCISANILWILNISFCGGIAEN 185 | |

FIG. 9

| | | | | | |
|---|---|---|---|---|---|
| | 1 | | | | 50 |
| Human | MKFTIVF.AG | LLGVFLAPAL | ANYNINVN.D | DNNNAGSGQQ | SVSVNNEHNV |
| Pig | MKFTIAF.AG | LLGVFLTPAL | ADYSISVN.D | DGNSGGSGQQ | SVSVNNEHNV |
| Mouse | MKLTM.FVVG | LLGLLAAPGF | A.YTVNINGN | DGNVDGSGQQ | SVSINGVHNV |
| | 51 | | | | 100 |
| Human | ANVDNNNGWD | SWNSIWDYGN | GFAATRLFQK | KTCIVHKMNK | EVMPSIQSLD |
| Pig | ANVDNNNGWN | SWNALWDYRT | GFAVTRLFEK | KSCIVHKMKK | EAMPSLQALD |
| Mouse | ANIDNNNGWD | SWNSLWDYEN | SFAATRLFSK | KSCIVHRMNK | DAMPSLQDLD |
| | 101 | | | | 150 |
| Human | ALVKEKKLQG | KGPGGPPPKG | LMYSVNPNKV | DDLSKFGKNI | ANMCRGIPTY |
| Pig | ALVKEKKLQG | KGPGGPPPKS | LRYSVNPNRV | DNLDKFGKSI | VAMCKGIPTY |
| Mouse | TMVKEQK..G | KGPGGAPPKD | LMYSVNPTRV | EDLNTFGPKI | AGMCRGIPTY |
| | 151 | | | 188 | |
| Human | MAEEMQEASL | FFYSGTCYTT | SVLWIVDISF | CGDTVEN | |
| Pig | MAEEIQGANL | ISYSEKCISA | NILWILNISF | CGGIAEN | |
| Mouse | VAEEIPGPNQ | PLYSKKCYTA | DILWILRMSF | CGTSVETY | |

FIG. 10

A mrgshhhhhhgs 21 NYNINVNDDNNNAGSGQQSVSVNNEHNVAN

51 VDNNNGWDSWNSIWDYGNGFAATRLFQKKTCIVHKMNKEVMPSIQSLDAL

101 VKEKKLQGKGPGGPPPKGLMYSVNPNKVDDLSKFGKNIANMCRGIPTYMA

151 EEMQEASLFFYSGTCYTTSVLWIVDISFCGDTVEN

B

A

```
HUMAN 1   MKFTIVFAGLLGVFLAPALANYNINVNDDNNNAGSGQQSVSVNNEHNVAN 50
  PIG 1   MKFTIAFAGLLGVFLTPALADYSISVNDDGNSGGSGQQSVSVNNEHNVAN 50

     51   VDNNNGWDSWNSIWDYGNGFAATRLFQKKTCIVHKMNKEVMPSIQSLDAL 100
     51   VDNNNGWNSWNALWDYRTGFAVTRLFEKKSCIVHKMKKEAMPSLQALDAL 100

    101   VKEKKLQGKGPGGPPPKGLMYSVNPNKVDDLSKFGKNIANMCRGIPTYMA 150
    101   VKEKKLQGKGPGGPPPKSLRYSVNPNRVDNLDKFGKSIVAMCKGIPTYMA 150

    151   EEMQEASLFFYSGTCYTTSVLWIVDISFCGDTVEN* 186
                                                  *=termination
    151   EEIQGANLISYSEKCISANILWILNISFCGGIAEN* 186
```

B

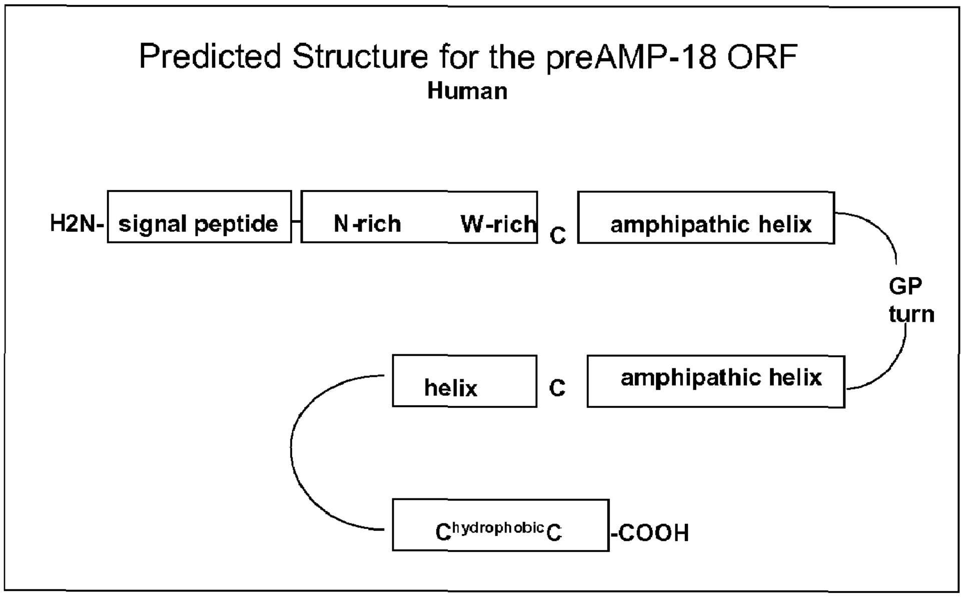

FIG. 14

GASTROKINES AND DERIVED PEPTIDES INCLUDING INHIBITORS

This application is a 35 U.S.C § 371 national stage application of PCT/US02/10148 filed Mar. 29, 2002, which claims priority to U.S. Ser. No. 09/821,726 filed Mar. 29, 2001.

BACKGROUND

A novel group of Gastric Antrum Mucosal Proteins that are gastrokines, is characterized. A member of the gastrokine group is designated AMP-18. AMP-18 genomic DNA, and cDNA molecules are sequenced for human and mouse, and the protein sequences are predicted from the nucleotide sequences. The cDNA molecule for pig AMP-18 is sequenced and confirmed by partial sequencing of the natural protein. The AMP-18 protein and active peptides derived from its sequence are cellular growth factors. Surprisingly, peptides capable of inhibiting the effects of the complete protein, are also derived from the AMP-18 protein sequence. Control of mammalian gastro-intestinal tissues growth and repair is facilitated by the use of the protein or peptides, making the protein and the derived peptides candidates for therapies.

Searches for factors affecting the mammalian gastro-intestinal (GI) tract are motivated by need for diagnostic and therapeutic agents. A protein may remain part of the mucin layer, providing mechanical (e.g., lubricant or gel stabilizer) and chemical (e.g against stomach acid, perhaps helping to maintain the mucus pH gradient and/or hydrophobic barrier) protection for the underlying tissues. The trefoil peptide family has been suggested to have such general cytoprotectant roles (see Sands and Podolsky, 1996). Alternatively, a cytokine-like activity could help restore damaged epithelia. A suggestion that the trefoil peptides may act in concert with other factors to maintain and repair the epithelium, further underlines the complexity of interactions that take place in the gastrointestinal tract (Podolsky, 1997). The maintenance of the integrity of the GI epithelium is essential to the continued well-being of a mammal, and wound closing after damage normally occurs very rapidly (Lacy, 1988), followed by proliferation and differentiation soon thereafter to reestablish epithelial integrity (Nusrat et al., 1992). Thus protection and restitution are two critical features of the healthy gastrointestinal tract, and may be important in the relatively harsh extracellular environment of the stomach.

Searches for GI proteins have met with some success. Complementary DNA (cDNA) sequences to messenger RNAs (mRNA) isolated from human and porcine stomach cells were described in the University of Chicago Ph.D. thesis "Characterization of a novel messenger RNA and immunochemical detection of its protein from porcine gastric mucosa," December 1987, by one of the present inventors working with the other inventors. However, there were several cDNA sequencing errors that led to significant amino acid changes from the AMP-18 protein disclosed herein. The protein itself was isolated and purified only as an aspect of the present invention, and functional analyses were performed to determine utility. Nucleic acid sequences were sought.

SUMMARY OF THE INVENTION

A novel gene product designated Antrum Mucosal Protein 18 ("AMP-18") is a gastrokine. The protein was discovered in cells of the stomach antrum mucosa by analysis of cDNA clones obtained from humans, pigs, and mice. The protein is a member of a group of cellular growth factors or cytokines, more specifically gastrokines. The AMP-18 cDNA sequences predict a protein 185 amino acids in length for both pig and man. The nucleotide sequences also predict a 20-amino acid N-terminal signal sequence for secreted proteins. The cleavage of this N-terminal peptide from the precursor (preAMP-18) was confirmed for the pig protein; this cleavage yields a secreted protein 165 amino acids in length and ca. 18,000 Daltons (18 kD) in size. Human and mouse genomic DNA sequences were also obtained and sequenced. A human genomic DNA was isolated in 4 overlapping fragments of sizes 1.6 kb, 3 kb, 3.3 kb and 1.1 kb respectively. The mouse genomic DNA sequence was isolated in a single BAC clone.

The gastrokine designated AMP-18 protein is expressed at high levels in cells of the gastric antrum. The protein is barely detectable in the rest of the stomach or duodenum, and was not found, or was found in low levels, in other body tissues tested. AMP-18 is synthesized in lumenal surface mucosal cells, and is secreted together with mucin granules.

Compositions of AMP-18 isolated from mouse and pig antrum tissue stimulate growth of confluent stomach, intestinal, and kidney epithelial cells in culture; human, monkey, dog and rat cells are also shown to respond. This mitogenic (growth stimulating) effect is inhibited by specific antisera (antibodies) to AMP-18, supporting the conclusion that AMP-18, or its products, e.g. peptides derived from the protein by isolation of segments of the protein or synthesis, is a growth factor. Indeed, certain synthetic peptides whose amino acid sequences represent a central region of the AMP-18 protein also have growth-factor activity. The peptides also speed wound repair in tissue culture assays, indicating a stimulatory effect on cell migration, the process which mediates restitution of stomach mucosal injury. Thus, the protein and its active peptides are motogens. Unexpectedly, peptides derived from sub-domains of the parent molecule can inhibit the mitogenic effect of bioactive synthetic peptides and of the intact, natural protein present in stomach extracts.

There are 3 activities of the gastrokine proteins and peptides of the present invention. The proteins are motogens because they stimulate cells to migrate. They are mitogens because they stimulate cell division. They function as cytoprotective agents because they maintain the integrity of the epithelium (as shown by the protection conferred on electrically resistant epithelial cell layers in tissue culture treated with damaging agents such as oxidants or non-steroidal anti-inflammatory drugs NSAIDs).

The synthesis of AMP-18 is confined to lumenal mucosal lining epithelial cells of the gastric antrum of humans and other mammals. Inside cells the protein is co-localized with mucins in secretion granules, and appears to be secreted into the mucus overlying the apical plasma membrane. Recombinant human AMP-18 in *E. coli* exerts its mitogenic effect at a concentration an order of magnitude lower than growth-promoting peptides derived from the center of the mature protein. Peptide 77-97, the most potent mitogenic peptide, is amino acid sequence-specific AMP peptides appears to be cell-type specific as it does not stimulate growth of fibroblasts or HeLa cells. Mitogenesis by specific AMP peptides appears to be mediated by a cell surface receptor because certain peptides that are not active mitogens can competitively inhibit, in a concentration-dependent manner, the growth-stimulating effects of peptide 58-99 and antrum cell extracts. AMP-18 and its derived peptides exhibit diverse effects on stomach and intestinal epithelial cells which suggest they could play a critical role in repair after gastric mucosal injury. These include cytoprotection, mitogenesis, restitution, and maturation of barrier function after oxidant-and/or indomethacin-mediated injury. Possible mechanisms by which AMP-18 or its peptide derivatives mediate their pleiotropic effects include stimulation of protein tyrosine kinase activity, prolongation of heat shock protein expression after cell stress, and enhanced accumulation of the tight junction-associated protein ZO-1 and occludin. Certain of these physiological effects can occur at concentrations that are relatively low for rhAMP-18 (<50 nM) compared to the concentrations of other gastric peptide mediators such as trefoil peptides or the α-defensin, cryptdin 3 (>100 μM). Immunoreactive AMP-18 is apparently released by cells of the mouse antrum after indomethacin gavage, and by canine antrum cells in primary culture exposed to forskolin, suggest that the protein is subject to regulation. These results imply that AMP-18 could play a role in physiological and pathological processes such as wound healing in the gastric mucosal epithelium in vivo.

The invention relates a group of isolated homologous cellular growth stimulating proteins designated gastrokines, that are produced by gastric epithelial cells and include the consensus amino acid sequence VKE(K/Q)KXXGKGPGG(P/A) PPK (SEQ ID NO: 10) wherein XX can be LQ or absent (which results in SEQ ID NOS: 25 and 26, respectively). An isolated protein of the group has an amino acid sequence as shown in FIG. 8. The protein present in pig gastric epithelia in a processed form lacking the 20 amino acids which constitute a signal peptide sequence, has 165 amino acids and an estimated molecular weight of approximately 18 kD as measured by polyacrylamide gel electophoresis. Signal peptides are cleaved after passage through endoplasmic reticulum (ER). The protein is capable of being secreted. The amino acid sequence shown in FIG. 3 was deduced from a human cDNA sequence. An embodiment of the protein is shown with an amino acid sequence as in FIG. 6, a sequence predicted from mouse RNA and DNA.

A growth stimulating (bioactive) peptide may be derived from a protein of the gastrokine group. Bioactive peptides rather than proteins are preferred for use because they are smaller, consequently the cost of synthesizing them is lower than for an entire protein.

In addition, a modified peptide may be produced by the following method:

(a) eliminating major protease sites in an unmodified peptide amino acid sequence by amino acid substitution or deletion; and/or (b) introducing into the modified amino acid analogs of amino acids in the unmodified peptide.

An isolated protein of the present invention include an amino acid sequence as in FIG. 8, present in pig gastric epithelia in a processed form lacking the 20 amino acids which constitute a signal peptide sequence, having 165 amino acids and an estimated molecular weight of approximately 18 kD as measured by polyacrylamide gel electophoresis, said protein capable of being secreted.

A protein of the present invention includes an amino acid sequence as in FIG. 3, a sequence deduced from a human cDNA.

A protein of the present invention includes an amino acid sequence as in FIG. 6, a sequence predicted from mouse RNA and DNA.

Embodiments of the present invention include a synthetic growth stimulating peptide, having a sequence of amino acids from positions 78 to 119 as shown in FIG. 3; having a sequence of amino acids from position 97 to position 117 as shown in FIG. 3, or a sequence of amino acids from position 97 to position 121 as shown in FIG. 3, or a sequence of amino acids from position 104 to position 117 as shown in FIG. 3.

An antibody to a protein of the present invention recognizies an epitope within a peptide of the protein that has an amino acid sequence from position 78 to position 119 as in FIG. 3.

An aspect of the invention also is an isolated genomic DNA molecule with the nucleotide sequence of a human as shown in FIG. 1 and an isolated cDNA molecule encoding a human protein with the amino acid sequence as shown in FIG. 3.

The invention includes a method to stimulate growth of epithelial cells in the gastrointestinal tract of mammals including the steps of:

(a) contacting the epithelial cells with a composition comprising a protein of the present invention or a peptide derived from the protein; and (b) providing environmental conditions for stimulating growth of the epithelial cells.

An embodiment of an isolated bioactive peptide has one of the following sequences:

```
KKLQGKGPGGPPPK,                (SEQ ID NO: 11)

LDALVKEKKLQGKGPGGPPPK,         (SEQ ID NO: 12)

LDALVKEKKLQGKGPGGPPPKGLMY.     (SEQ ID NO: 13)
```

Embodiments of inhibitors are

```
KKTCIVHKMKK                 (SEQ ID NO: 14)

or

KKEVMPSIQSLDALVKEKK.        (SEQ ID NO: 15)

(see also Table 1)
```

Antibodies to the protein product AMP-18 encoded by the human cDNA expressed in bacteria were produced in rabbits; these antibodies reacted with 18 kD antrum antigens of all mammalian species tested (human, pig, goat, sheep, rat and mouse), providing a useful method to detect gastrokines. An antibody to a protein of the group recognizes an epitope within a peptide of the protein that includes an amino acid sequence from position 78 to position 119 as in FIG. 3.

The invention is also directed to an isolated genomic DNA molecule with the nucleotide sequence of a human as shown in FIG. 1 and an isolated cDNA molecule encoding a human protein, that the nucleotide sequence as shown in FIG. 2.

Another aspect of the invention is an isolated DNA molecule having the genomic sequence found in DNA derived from a mouse, as shown in FIG. 4.

Genomic DNA has value because it includes regulatory elements for gastric expression of genes, consequently, the regulatory elements can be isolated and used to express other gene sequences than gastrokines in gastric tissue.

An aspect of the invention is a method to stimulate growth of epithelial cells in the gastrointestinal tract of mammals. The method includes the steps of:

(a) contacting the epithelial cells with a composition comprising a gastrokine protein or a peptide derived from a protein of the group; and (b) providing environmental conditions for stimulating growth of the epithelial cells.

A method to inhibit cellular growth stimulating activity of a protein of the group includes the steps of:

(a) contacting the protein with an inhibitor; and (b) providing environmental conditions suitable for cellular growth stimulating activity of the protein.

The inhibitor may be an antibody directed toward at least one epitope of the protein, e.g. an epitope with an amino acid sequence from position 78 to position 119 of the deduced amino acid sequence in FIG. 3 or an inhibitor peptide such as those in Table 1.

A method of testing the effects of different levels of expression of a protein on mammalian gastrointestinal tract epithelia, includes the steps of:

(a) obtaining a mouse with an inactive or absent gastrokine protein;
(b) determining the effects of a lack of the protein in the mouse;
(c) administering increasing levels of the protein to the mouse; and
(d) correlating changes in the gastrointestinal tract epithelia with the levels of the protein in the epithelia.

Kits are contemplated that will use antibodies to gastrokines to measure their levels by quantitative immunology. Levels may be correlated with disease states and treatment effects.

A method to stimulate migration of epithelial cells after injury to the gastrointestinal tract of mammals, includes the steps of:

(a) contacting the epithelial cells with a composition comprising a peptide derived from the protein; and
(b) providing environmental conditions allowing migration of the epithelial cells.

A method for cytoprotection of damaged epithelial cells in the gastrointestinal tract of mammals, includes the following steps:

(a) contacting the damaged epithelial cells with a composition including a protein of the gastrokine group or a peptide derived from the protein; and
(b) providing environmental conditions allowing repair of the epithelial cells.

The damaged cells may form an ulcer.

BRIEF DESCRIPTION OF THE DRAWINGS

FIG. 1 is a human genomic nucleotide sequence (SEQ ID NO: 1) of a pre-gastrokine; sequence features were determined from cDNA and PCR of human genomic DNA amphge8.seq Length: 7995 predicted promoter: 1405; exon 1: 1436-1490; exon 2: 4292-4345; exon 3: 4434-4571; exon 4: 5668-5778; exon 5: 6709-6856; exon 6: 7525-7770; polyA site: 7751.

FIG. 2 is a human cDNA sequence (SEQ ID NO: 2); the DNA clone was obtained by differential expression cloning from human gastric cDNA libraries.

FIG. 3 is a human preAMP-18 protein sequence (SEQ ID NO: 3) predicted from a cDNA clone based on Powell (1987) and revised by the present inventors; N-21 is the expected N-terminus of the mature protein.

FIG. 4 is a mouse preAMP-18 sequence (SEQ ID NO: 4) determined from RT-PCR of mRNA and PCR of BAC-clones of mouse genomic DNA sequences:

predicted promoter: 1874 experimental transcription start site: 1906 translation initiation site: 1945 CDS 1: 1906-1956; CDS 2: 3532-3582; CDS 3: 3673-3813; CDS 4: 4595-4705; CDS 5: 5608-5749; CDS 6: 6445-6542; polyA site: 6636.

FIG. 5 is a mouse cDNA sequence (SEQ ID NO: 5) for preAMP-18.

FIG. 6 is mouse preAMP-18 amino acid sequence (SEQ ID NO: 6); RT-PCR performed on RNA isolated from mouse stomach antrum: Y-21 is the predicted N-terminus of the mature protein; the spaces indicated by . . mean there are no nucleotides there to align with other sequences in FIG. 11.

FIG. 7 is a cDNA expressing porcine AMP-18 (SEQ ID NO: 7).

FIG. 8 is pig pre-gastrokine (pre-AMP-18) protein sequence (SEQ ID NO: 8) predicted from a cDNA clone based on Powell (1987) D-21 is the N-terminus of the mature protein-confirmed by sequencing of the protein isolated from pig stomach.

FIG. 9 is a comparison between the amino acid sequences of human (SEQ ID NO: 3) versus pig (SEQ ID NO: 8) pre-gastrokine.

FIG. 10 shows a computer-generated alignment comparison of human (SEQ ID NO: 3), pig (SEQ ID NO: 8) and mouse (SEQ ID NO: 6) predicted protein sequences determined from sequencing of cDNA clones for human and pig AMP-18, and by polymerase chain reaction of mouse RNA and DNA using preAMP-18 specific oligonucleotide primers; in each case the first 20 amino acids constitute the signal peptide, cleaved after passage through the endoplasmic reticulum membrane.

Figure 11:
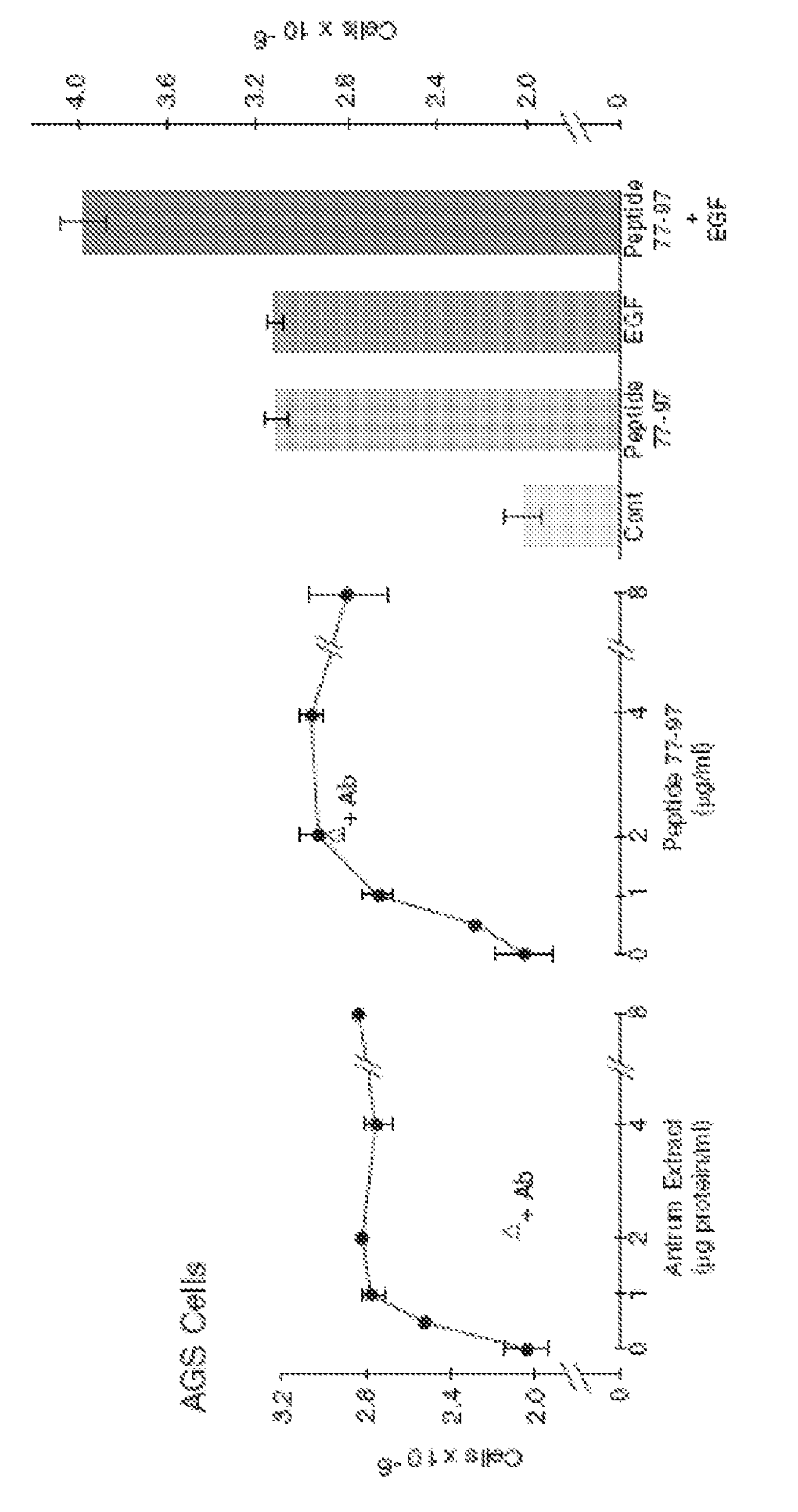

FIG. 11 shows the effect of porcine gastric antrum mucosal extract, human AMP peptide 77-97 (of the mature protein, same as peptide 97-117 of human precursor protein; Table 1), and EGF on growth of gastric epithelial cells; AGS cells were grown in DMEM containing fetal bovine serum (5%) in 60-mm dishes; different amounts of pig antrum extract, HPLC purified peptide 77-97, and/or EGF were added; four days later the cells were dispersed and counted with a hemocytometer; antrum extract and peptides each stimulated cell growth in a concentration-dependent manner; the bar graph shows that at saturating doses, peptide 77-97 (8 μg/ml) or EGF (50 ng/ml) was mitogenic; together they were additive suggesting that the two mitogens act using different receptors and/or signaling pathways; anti-AMP antibodies inhibited the antrum extract but did not inhibit peptide 77-97.

Figure 12:
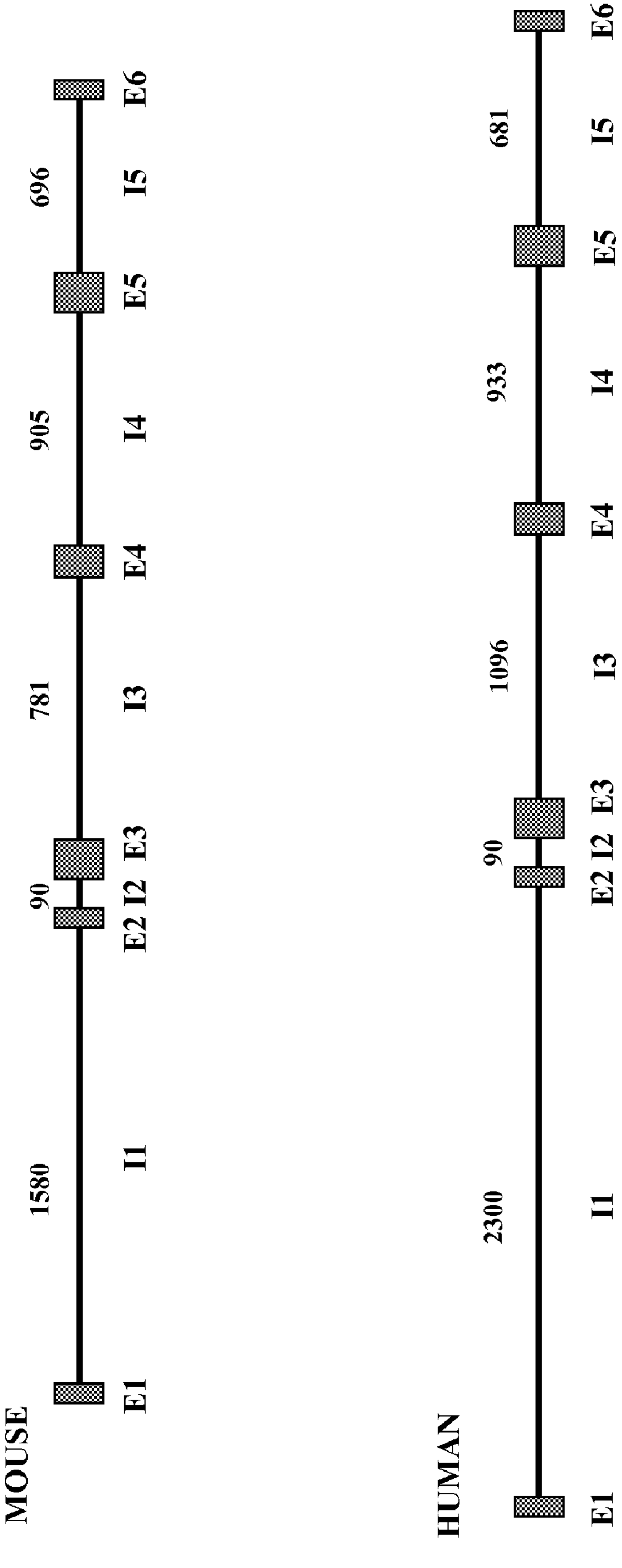

FIG. 12 shows the structure of the human and mouse preAMP-18 genes; the number of base pairs in introns are shown above the bars; exons are indicated E1-E6 and introns I1-I5; there are minor differences in intron length.

Figure 13:
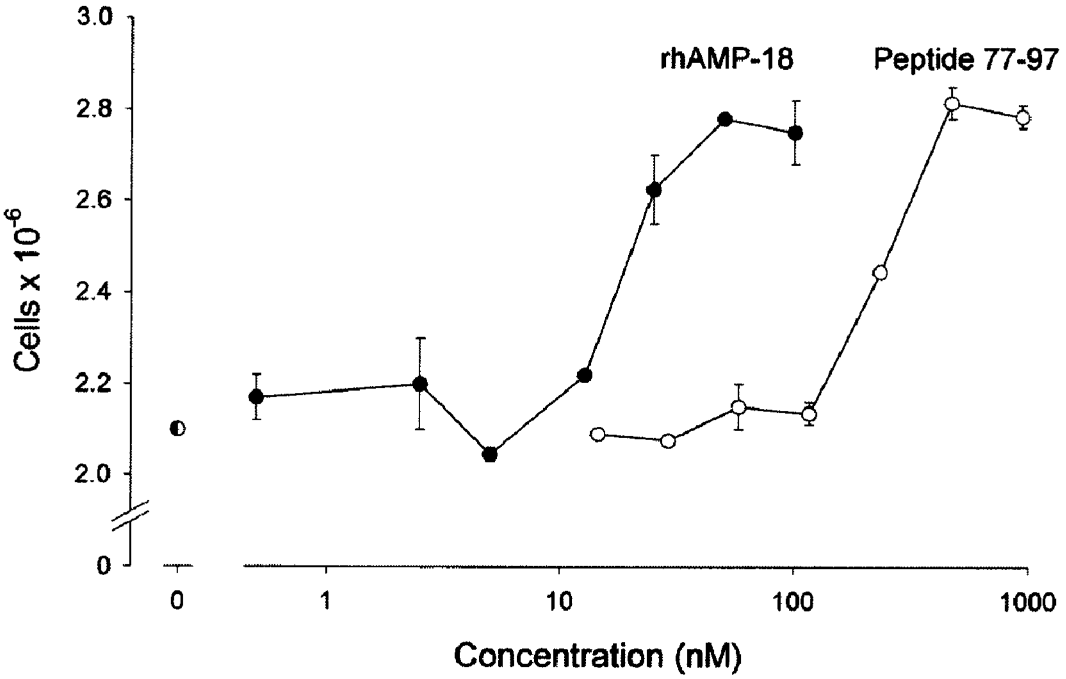

FIG. 13 shows Left panel. Amino acid sequence of recombinant human AMP-18 (residues 21 to 185 of SEQ ID NO: 3) expressed in *E. coli*. Note the His6-tag (SEQ ID NO: 16) within a 12 amino acid domain (SEQ ID NO: 9) at the N-terminus that has replaced the putative hydrophobic signal peptide. Right panel. Effect of rhAMP-18 and AMP peptide 77-97 on growth of confluent cultures of IEC-18 cells. Although maximal growth stimulation is similar, the half-maximal concentration ($K_{1/2}$) for rhAMP-18 (~30 nM) is about an order of magnitude lower than for the peptide (~300 nM).

FIG. 14 shows Left Panel. Alignment of the open reading frames (ORF) derived from the cDNA clones for AMP-18 for the precursor proteins of human (SEQ ID NO: 3) and pig (SEQ ID NO: 8) antrum. Similarity was 78.50% and identity was 75.27%. Computer analysis was carried out using the GAP and PEPTIDESTRUCTURE programs of the Wisconsin Package (GCG). Right Panel Model of the predicted secondary structure for the human preAMP ORF. Attention is drawn to the asparagine rich N-terminal domain, the short tryptohopan (W)-rich and glycine-proline (GP) regions, and the conserved positions of the four cysteine (C) residues. Possible amphipathic helices are indicated.

DETAILED DESCRIPTION OF THE INVENTION

1. General

A novel gene product, a member of a group of gastrokines, was detected in mammalian gastric antrum mucosal by a differential screen of cDNA libraries obtained from different regions of the pig stomach. The cDNA sequence predicted a protein of 185 amino acids including a signal peptide leader sequence. A cDNA was also isolated from a human library. The predicted amino acid sequence identity between pig and human in 76.3%. The sequences predicted a 20 amino acid signal peptide characteristic for secreted proteins. The cleavage of this N-terminal signal peptide was confirmed for the pig protein. Antibodies to the product of the human cDNA expressed in bacteria were raised in rabbits; these antibodies reacted with 18-20 kD antrum antigens of all mammalian species tested (pig, goat, sheep, rat and mouse). In agreement with mRNA levels, the AMP-18 protein is expressed at high levels only in the gastric antrum; it is barely detectable in the rest of the stomach or duodenum, and was not detected in a variety of other tissues tested. AMP-18 is synthesized in the lumenal surface mucosal cells; immuno-electron microscopy locates AMP-18 in the secretion granules of these cells. Partially purified AMP-18 preparations from mouse and pig antrum tissue are mitogenic to confluent stomach and kidney epithelial cells in culture; this effect is inhibited by the specific antisera, implying that AMP-18, or its products, is a growth factor.

AMP-18 is likely secreted with the mucus and functions, perhaps as peptide derivatives, within the mucus gel to maintain epithelial integrity directly, and possibly to act against pathogens. In view of the growth factor activity observed on epithelial cell lines in culture, it is likely that AMP-18 or its peptide derivative(s) serves as an autocrine (and possible paracrine) factor for the gastric epithelium. The function of AMP-18 may not be simply as a mitogen, but in addition it may act as differentiation factor providing the signals for replenishment of the mature lumenal surface cells. The AMP-18 protein or its derivatives are likely important to the normal maintenance of the highly dynamic gastric mucosa, as well as playing a critical role in the restitution of the antrum epithelium following damage. This protein has not been characterized in any publication, however, related nucleic acid sequences have been reported as ESTs and as a similar full length gene. Limitations of EST data cannot yield information on starting sequences, signal peptides, or sequences in the protein responsible for bioactivity, as disclosed in the present invention. A number of these ESTs have been reported for mammalian stomach cDNAs, but related ESTs have also been reported or pancreas and also pregnant uterus libraries. Although expression of AMP-18 RNA in these other tissues appears to be low (as indicated for pancreas by PCR analysis), these results suggest that this growth factor may have broader developmental and physiological roles than that implied by the specific high levels of expression found for the stomach.

The AMP-18 protein appears to be expressed at the surface of the cellular layers of the gastrointestinal (GI) tract. The expressing cells may be releasing stored growth factor where needed—in the crypts and crevices of the GI tract where cellular repair is needed due to surface damage.

AMP-18 may act on the mucosal, apical surfaces of the epithelial cells, collaborating with prostaglandins and other growth factors that operate via basolateral cell surface receptors on the serosal side. The protein or its derivatives are likely important for the normal maintenance of the highly dynamic gastric mucosa, in face of the mechanical stress and high acidity of the stomach. AMP-18 may play a critical role in the repair of the stomach epithelium following damage by agents such as alcohol, nonsteroidal anti-inflammatory drugs (NSAIDs), or pathogens, in particular *Heliobacter pylori*, which predominantly infects the antrum and is a causative agent of gastric ulcers and possibly cancers.

2. Bioactivity

A synthetic peptide (42 amino acids, a “42-mer”) representing a central region of the AMP-18 amino acid sequence also has growth factor activity, which is inhibited by specific antisera; some related shorter peptides also have stimulatory activity, while others can inhibit the activity of the 42-mer. This result suggests that a saturatable epithelial receptor exists for AMP-18, and opens direct avenues to analyzing the bioactive regions of the protein and identifying the putative receptor(s). Because AMP-18 does not resemble in structure any known cytokine or cytoprotectant protein (such as the trefoil peptides), the analysis of the interactions of the protein, and its active and inhibitory related peptides, with cells offers the opportunity to reveal novel molecular interactions involved in cell growth control.

BSC-1 cell growth was stimulated by gel-fractionated porcine antrum extract; porcine extract protein (250 μg) was loaded into each of 2 lanes and subjected to electrophoresis in a polyacrylamide gel (12.5%); the 5 thin slices (2-3 mm) from each area between $M_r$ 14 kDa and 21.5 kDa were cut from the experimental lanes. Each pair of slices was placed in a silanized microfuge tube with 200 μl sterile PBS, 3% acetonitrule and 1% BSA, and macerated; proteins were eluted from the gel for 18 hr at 22° C. with vigorous shaking; the samples were then microcentrifuged and a sample of a supernatant was added to a confluent culture of BSC-1 cells; the number of cells was counted 4 days later; maximal growth stimulation was observed in cultures receiving extracts eluted from gel slices corresponding to a $M_r$ of 18 kDa; antisera to recombinant human AMP-18 added to the culture medium completely inhibited growth stimulation by the 18 kDa fraction (+Ab); values are means of 2 cultures; SE is less than 10% of the mean.

The biological activity (mitogenic for epithelial cells in the gastro-intestinal tract) of the AMP-18 is located in the C-terminal half of the protein. The epitopic sequence(s) appear(s) to be immediately N-terminal to the mitogenic sequence.

The biological activity that is a growth factor, is exhibited by a peptide comprising at least 42 amino acids from positions 78 to 119 of the full-length protein sequence (see Table 1). An antibody to this region blocked mitogenic activity. Although a peptide having an amino acid sequence of 104 to 117 had mitogenic activity, an antibody to this region did not block (inhibit) the activity. A peptide with an amino acid sequence from positions 97-117 has the same mitogenic activity as a peptide with the 42 amino acid sequence, but is less expensive to produce as a synthetic peptide.

3. Inhibition of Bioactivity

Epithelial cell growth that was stimulated by murine or porcine antrum cell extract was blocked by rabbit antiserum to a complete, recombinant human AMP-18 precursor protein; confluent cultures of BSC-1 cells were prepared; murine or porcine antrum cell extract was prepared and its protein concentration was measured; cell extracts alone and with different dilutions of the antiserum, or antiserum alone (1:100 dilution was added to the culture medium, and the number of cells was counted 4 days later). Growth stimulation by murine antrum gastrokines was maximally inhibited by the antiserum (93%) at a dilution of 1:400, whereas stimulation by the porcine antrum protein extract was totally inhibited at a dilution of 1:100. Scored values were means for 3 cultures; standard error of the mean (SE) was less than 10% of the mean.

Antibodies to the AMP-18 protein have diagnostic uses to determine different levels of the protein in the gastro-intestinal tract in vivo. Ulcers are likely to develop if less than normal levels of AMP-18 protein are present. Normal values are determined by technologies known to those of skill in the art, that is, obtaining representative samples of persons to be tested (age, sex, clinical condition categories) and applying standard techniques of protein quantitation. The effects of aspirin and indamethacin on AMP-18 levels are also useful to monitor deleterious levels of the drugs including the non-steroidal anti-inflammatory drugs (NSAIDs). Stomach cancer cell lines do not express the AMP-18 proteins at least by detection methods disclosed herein.

4. Genomic DNA

Genomic AMP-18 DNA sequences have been cloned for human and mouse as a prelude to the analysis of the gene regulatory elements, which presumably determine the great differences in the levels of expression of the gene in tissues where the gene may be active. Upstream and downstream flanking sequences have been isolated from mouse genomic DNA preparatory to a gene knockout. The flanking genomic sequences likely determine the very different levels of expression of the gene in the stomach and few other tissues where it may be expressed. With the involvement of different regulatory elements, gastrokine genes could be expressed as a growth factor in other tissues.

5. Uses of Gastrokines of the Present Invention

Because the AMP-18 protein and certain peptides derived from it can stimulate growth and wound repair by stomach and intestinal epithelial cells (as well as kidney) these gastrokine molecules are candidates for therapeutic agents to speed recovery of the injured GI tract following pharmacological interventions, radiotherapy, or surgery. In addition, the antibodies developed to gastrokines may be used in kits to measure the levels of AMP-18 protein or peptide in tissue of blood in diverse pathological states. These novel molecules have great therapeutic potential in the treatment of gastric ulcers, and inflammatory bowel disease, whereas new agents that inhibit its function could prove useful in the treatment of cancers of the GI tract.

The stomach is not a congenial location for many bacteria, and those that can survive the acidity do not establish themselves there (Rotimi et al., 1990). It is of interest therefore that the antrum region is the favored site for the attachment, penetration and cytolytic effects of *Helicobaccter pylori*, an agent which infects a major proportion of the human population (>60% by the seventh decade) and has been associated with gastritis, gastric and duodenal ulcers (Goodwin et al., 1986; Blaser, 1987) and gastric adenocarcinomas (Nomura et al., 1991; Parsonnet et al., 1991). Thus as an epithelial cell growth factor, AMP-18 may act to ameliorate the damage caused by bacterial infiltration and cytolysis. Given the conjunction of the specific antrum expression of AMP-18 and the preferred site of binding of *H. pylori*, it is possible that the bacteria use AMP-18 as a tropic factor. *H pylori* attaches to cells of the antrum having fucose-containing mucin granules (Falk et al., 1993; Baczako et al., 1995). These granules also may contain AMP-18. Anti-microbial peptides have been found in the stomach of the amphibian *Xenopus laevis* (Moore et al., 1991). Some domains of the AMP-18 structure resemble that of the magainins, and possibly AMP-18 interacts with enteric bacteria.

6. Isolation of Pig AMP-18

Antisera against human AMP-18 protein were used to assist in the purification of the protein from extracts of pig antrum mucosa. Immunoaffinity methods applied to total tissue extracts have not proven very effective, but by using immunoblots to monitor cell-fractionation, gradient centrifugation and gel electrophoresis sufficient amounts of the pig 18 kDa polypeptide was purified to confirm by sequencing that the native N-terminus is the one predicted by cleavage of 20 amino acids from the N-terminus of the ORF precisely at the alanine-aspartate site anticipated for signal peptide removal. Despite the abundance of asparagine residues in the mature protein, none fit the consensus context characteristic of glycosylation. Fairly extensive regions of the protein may possess amphipathic helix forming propensity. The latter may represent units within the protein yielding bioactive peptides after processing. Using circular dichroism the synthetic peptide representing amino acids 126-143 in the human preAMP sequence (FIG. 3) is readily induced to become helical in moderate concentrations of trifluoroethanol conditions used to assess helix propensity for some bioactive peptides, including anti-microbial peptides of the magainin type (see, for example, Park et al., 1997).

7. Preparation of active recombinant human AMP-18 in *E. coli*

A cDNA encoding human AMP-18 was designed in which the 20-amino acid hydrophobic signal peptide sequence was replaced with an N-terminal 12-amino acid peptide that included a stretch of 6 histidine residues (FIG. 13, left panel). Expression of this modified cDNA sequence was predicted to yield a 177-amino acid protein product ($M_r$, 19, 653) that could be readily purified using Ni—NTA resin to bind the His6-tag (SEQ ID NO: 16). The cDNA sequence lacking the region coding for the N-terminal signal peptide (see FIG. 14) was amplified by PCR using oligonucleotides that provided suitable linkers for inserting the product into the BamH1 site of a QE30 expression vector (QIAGEN); the sequence of the recombinant vector was confirmed. The recombinant human (rh) AMP-18 engineered with the His6-tag (SEQ ID NO: 16) was subsequently expressed in *E. coli* cells. To harvest it, the bacteria were lysed and alquots of the soluble and insoluble fractions were subjected to SDS-PAGE followed by immunoblotting using the specific rabbit antiserum to the rhAMP-18 precursor. Very little of the expressed protein was detected in the soluble fraction of the lysate.

Urea (6 M) was employed to release proteins from the insoluble fraction solubilize rhAMP-18 containing the His6-tag (SEQ ID NO: 16), and make it available to bind to the $Ni^{2+}$-charged resing from which it was subsequently eluted with a gradient of imidazole (0 to 200 mM). The amount of eluted rhAMP-18 was measured using the BCA assay, and the appearance of a single band at the predicted size of 19-20 kD was confirmed by SDS-PAGE followed by immunoblotting. To determine if eluted rhAMP-18 renatured to assume a structure that was mitogenic, aliquots of the eluate (following removal of urea and imidazole by dialysis) were added to cultures of IEC-18 cells and the number of cells was counted 4 days later. FIG. 13 (right panel) indicates that the recombinant protein stimulates cell proliferation to the same maximal extent as does mitogenic AMP peptide 77-97 (or soluble antrum tissue extracts from pig shown in FIG. 1), but that it does so at a half-maximal concentration an order of magnitude lower than for peptide 77-97. AMP peptide 77-97 refers to the mature protein; same as peptide 97-117 of human precursor protein in Table 1. These observations indicate that biologically active recombinant human AMP-18 that can be utilized in diverse clinical situations is available. The mitogenic potency of rhAMP-18 is in the nanomolar range which would be expected for a native gastric cell growth factor that participates in the maintenance and repair of the stomach in vivo.

Materials and Methods

1. Isolation of Antrum-Specific cDNA Clones cDNA clones for the gastrointestinal (GI) peptide gastrin, which regulates gastric acid secretion as well as mucosal and pancreatic cell growth (Yoo et al., 1982) were isolated. From these screens several other mRNAs expressed relatively specifically in the antrum of the stomach were found. The open reading frame (ORF) in one of these RNAs was highly conserved between pig and man, and predicted a novel conserved protein of no immediately apparent function. Using specific antibodies, it was shown that similar protein species are present in the stomach antrum mucosa of all mammals tested. There is tissue specificity of expression of these sequences and they are apparently ubiquitously present in the antrum mucosa of mammalian species.

2. RNA Expression

The isolation of the cDNA clones was predicted on a preferential expression in the mucosa of the stomach antrum and this has been confirmed initially by Northern blot hybridization of RNAs from various tissues probed with the cDNA sequences and subsequently by protein analysis. The Northern blots showed the specificity of mRNA expression within the gastrointestinal tract of the pig. Highest mRNA expression was in the antrum mucosa, variable amounts in the adjacent corpus mucosa and undetectable levels in fundus, esophagus and duodenum. The non-mucosal tissue of the antrum and corpus contained little RNA reacting with the cDNA probe.

3. Antibodies to Expressed Protein

The open reading frames (ORFs) of the human and pig cDNA clones predict very similar relatively low molecular weight (MW) proteins, which have no close homologs to known proteins in the computer databases and therefore give little indication of possible function. As an approach to study the biological role of the presumptive proteins, the full cDNA sequences were expressed in *E. coli*, using a vector that also encoded an N-terminal His6-tag (SEQ ID NO: 16). Unfortunately, as expressed in bacteria the polypeptide products are insoluble and not readily amenable to biochemical studies. However, the bacterial product of the human cDNA was separated on sodium dodecyl sulfate (SDS) gels used as an immunogen in rabbits to elicit antisera. The sera were screened against protein extracts of antral tissue from a number of mammalian species. This procedure has successfully produced several high-titer, low background antisera capable of recognizing both the immunogen and proteins of about 18 kDa expressed in the antrum of the mammals tested. The bacterially-expressed protein migrates more slowly because it contains the signal peptide sequence was well as a His6-tag (SEQ ID NO: 16). The preimmune sera showed no significant 18 kDa reactivity. The cross-reactivity of the antisera raised against the protein expressed from the human cDNA clone with proteins of very similar MW in antrum extracts from a variety of mammals (pig, goat, sheep, rat and mouse; the last consistently migrates slightly more rapidly in SDS gels) supports the level of conservation of amino acid sequence predicted by comparison of the ORFs of the human and pig cDNAs (See FIG. 10). In subsequent experiments, human AMP-18 with a signal peptide was produced in bacteria.

The preimmune sera give insignificant reactions on Western blots of all tissue extracts, while the two immune sera (at up to 1:50000 dilution) both give major bands of 18-20 kDa only, and those only in stomach antrum extracts, and to a lesser degree in the adjacent corpus extracts. The sera were raised against bacterially-expressed protein so there is no possibility of other exogenous immunogens of animal origin.

As determined by immunoblots, the specificity of expression to the antrum is even greater than the Northern blots would suggest, and the strength of the signal from antrum extracts implies a relatively high abundance of the protein, although quantitative estimates were not made. Significant antigen was not detected in non-stomach tissues tested.

The immunohistochemistry showed insignificant staining of antral tissue by both preimmune sera, while both immune sera stained the surface mucosal cells very strongly at considerable dilutions. The preimmune sera did not lead to immunogold staining in the immunoelectron microscope study. The growth factor activity of antrum extracts is inhibited by both immune, but not preimmune sera. Finally, the results with a synthetic peptide, which has growth factor activity, is inhibited by the immune but not the preimmune sera, and carries epitopes recognized by the immune but not the preimmune sera, further validate the specificity of these reagents.

4. Northern Blot Hybridization of RNAs From Pig Gut Mucosal Tissues

Total RNA was electrophoresed, transferred to a membrane and hybridized with a labeled pig AMP-18 cDNA probe. The source of the RNA sample for each lane was: 1. Distal duodenum; 2. Proximal duodenum; 3. Antrum; 4. Adjacent corpus; 5. Fundus; 6. Esophagus. Equal amounts of RNA were loaded. The signal from RNA of the antrum adjacent corpus was variable. Size markers (nucleotides) were run on the same gel for comparison.

5. Immunoblots Using A Rabbit Antiserum Raised Against the Bacterial-Expressed Protein Directed By the Human Antrum-Specific cDNA Clone Whole tissue proteins were dissolved in SDS buffer, electrophoresed, and transferred to membranes that were reacted with immune serum (1:50000). Bound antibody molecules were detected using peroxidase-labeled anti-rabbit antibody. Preimmune serum gave no specific staining of parallel blots at 1:200 dilution. Lanes: 1,6,13,17 contained markers. 2 HeLa cells. 3 mouse TLT cells. 4 expressed human protein +HELA cells. 7 mouse corpus. 8 mouse antrum. 9 mouse duodenum. 10 mouse intestine. 11 mouse liver. 12 expressed human protein +TLT cells. 14 mouse antrum. 15 mouse brain. 16 mouse Kidney. 18 pig antrum. 19 mouse antrum.

Immunoblots of high percentage acrylamide gels showed that the antisera recognized epitopes on the synthetic peptide 78-119. The reaction of peptide 78-119 with the antibodies was not unexpected because this region of the sequence was predicted to be exposed on the surface of the protein and to be antigenic. Not only does this further substantiate a belief that AMP-18 or its immediate precursor, is a growth factor, for epithelial cells, but also provides a basis for analysis of the bioactive (and antigenic) regions of AMP-18, and a tool for the assessment of cell receptor number and identity. Chemical synthesis of peptides also makes available a convenient and rapid source of considerable quantities of pure “wild-type” and “mutant” reagents for further cell studies. The synthetic peptide 78-119 apparently acts by the same mechanism as the antrum protein, because their maximal effects are not additive.

6. Sequence and Predicted Structure of the Pre-AMP Open Reading Frame

The predicted amino acid sequences for human and pig are 76% identical. The predicted signal peptides are not bold; the N-terminus of native pig AMP has been shown to be aspartate (FIG. 10).

7. Structure of the Native Protein

The ORF's of the human and pig cDNAs predicted polypeptides of similar general structure (FIG. 10). The predicted molecular weights for the otherwise unmodified human and pig proteins was 18.3 and 18.0 respectively; these values are in good agreement with electrophoretic mobility in SDS the of antrum proteins reacting with the antisera of the present invention.

The antisera was used to assist in the purification of the protein from extracts of pig antrum mucosa. Immunoaffinity methods applied to total tissue extracts have not proven very effective, but by using immunoblots to monitor cell-fractionation, gradient centrifugation and gel electrophoresis sufficient amounts of the pig 18 kDa polypeptide was purified to confirm by sequencing that the native N-terminus is one predicted by cleavage of about 20 amino acids from the N-terminus of the ORF precisely at the alanine-aspartate site anticipated for signal peptide removal. Despite the abundance of asparagine residues, none fit the consensus context for glycosylation. Fairly extensive regions which may possess amphipathic helix forming propensity. The latter may represent units within the protein or as peptides after processing. Using circular dichroism the synthetic peptide representing amino acids 126-143 in the human preAMP sequence (FIG. 3) is readily induced to become helical in moderate concentrations of trifuoroethanol conditions used to assess helix propensity for some bioactive peptides, including anti-microbial peptides of the magainin type (see for example Park et al., 1997).

8. Localization of AMP-18

The antisera to AMP-18 have proven to be excellent histochemical probes, reacting strongly with sections of the mouse antrum region but not with the fundus, duodenum or intestine, confirming the results of the immunoblots. The preimmune sera give negligible reactions even at much higher concentration. The AMP-18 protein appears to be concentrated in mucosal epithelial cells lining the stomach lumen, although lesser signals in cells deeper in the tissue and along the upper crypt regions suggest that cells may begin to express the protein as they migrate toward the lumenal layer. Higher magnification of the histochemical preparations indicates only a general cytoplasmic staining at this level of resolution; there are some patches of intense staining that may be the light microscope equivalent of granule-packed regions of some lumenal surface cells seen by electron microscopy (EM). The localization of AMP-18 in the antrum mucosa is therefore very different from those cells synthesizing gastrin which are deep in the mucosal layer.

9. Immunoelectron microscope localization of the AMP-18 antigens in the mouse stomach antrum mucosal cells The tissue pieces were fixed in 4% formaldehyde and processed for embedding in Unicryl. Thin sections were reacted with rabbit anti-human AMP-18 antisera (1:200); bound antibodies detected by Protein-A conjugated to 10 nm colloidal gold. The reacted sections were stained with lead citrate before viewing (20,000×). The gold particles are visible over the semi-translucent secretion granules, which appear much more translucent here than in the standard glutaraldehyde-osmium-epon procedure (11,400×) because of the requirements for immuno-reactivity. Negligible background was seen on other cytoplasmic structures.

The general structure of the protein implies a possible secretory role so a precise intracellular localization would be valuable. This requires EM immuno-cytochemical procedures. Standard embedding and staining methods reveal that, as previously reported by many others, the antrum region (e.g. Johnson and McMinn, 1970) contains mucosal epithelial cells which are very rich in secretory granules. Preliminary immuno-EM data show the immune sera used at 1:200-1:800 dilution react specifically with the secretion granules. The latter appear somewhat swollen and less electron opaque than in standard fixation conditions and the differences in density are harder to discern, but overall the cell structure is quite well-preserved for 30 stomach tissue fixed and embedded under the less stringent conditions required to preserve immuno-reactivity. At 1:100 dilution, the preimmune sera exhibited negligible backgrounds with no preference for the secretion granules.

10. Growth Factor Activity on Epithelial Cell Cultures.

A possible function for AMP-18 is that it is a growth factor at least partly responsible for the maintenance of a functional mucosal epithelium in the pyloric antrum and possibly elsewhere in the stomach. Initially, stomach epithelial cell lines were not immediately available, but kidney epithelial cell systems (Kartha et al., 1992; Aithal et al., 1994; Lieske et al., 1994) were used. A fractionated antrum mucosal cell extract was used for these experiments. Using immunoblotting as a probe to follow fractionation, on lysis of the mucosal cells scraped from either pig or mouse antrum, the AMP-18 antigen was recovered in the 35S fraction on sucrose density gradients. Such high speed supernatant fractions served as the starting material for studies on cell growth. Unexpectedly, these extracts stimulated a 50% increase in confluent renal epithelial cells of monkey (BSC-1 cells), but had no effect on HeLa or WI-38 fibroblast cells. The stimulation of BSC-1 cells was at least as effective as that observed with diverse polypeptide mitogens, including EGF, IGF-I, aFGF, bFGF and vasopressin, assayed at their optimal concentrations. Comparable growth stimulation by the antrum extracts was observed when DNA synthesis was assessed by measuring [$^3$H]thymidine incorporation into acid-insoluble material. The biological activity of the antrum extracts survived heating for 5 minutes at 65° C., and dialysis using a membrane with $M_r$ cutoff of 10 kDa, which would eliminate most oligopeptides; this treatment removes 60-70% of polypeptide material, but spared AMP-18 as assayed by immunoblots. More importantly, mitogenic stimulation of BSC-1 cells by the mouse or pig antrum extract was inhibited when either of two different antisera to the human recombinant preAMP-18 (expressed in bacteria) was added to the culture medium. Preimmune sera (1:100 to 1:800) had no effect on cell growth, nor did they alter the mitogenic effect of the antrum extracts. These observations suggest that gastric mucosal cell AMP-18 functions as a potent mitogen for kidney epithelial cells, which do not normally express this protein.

To gain further evidence that the growth-promoting activity in the partially fractionated antrum extracts was mediated by the AMP-18 protein, an aliquot of the mouse extract was subjected to SDS-polyacrylamide gel electrophoresis; the method used previously to determine the N-terminal sequence of the natural protein. The gel was cut into 2-mm slices and each slice was extracted with 3% acetonitrile in phosphate-buffered saline containing 1% BSA. The extract supernatants were assayed for mitogenic activity. The results indicated that one slice containing protein in the 16-19 kDa range possessed growth-promoting activity. Significantly, this growth response was blocked by the immune but not the pre-immune sera. Taken together with the relatively low sedimentation rate of the protein, these findings provide additional evidence to support the conclusion that AMP-18 is an epithelial cell mitogen and that it functions as a monomer or possibly a homotypic dimer. It also implies that the structure of the protein is such that it can readily reacquire a native conformation after the denaturing conditions of SDS-gel electrophoresis.

To assess the interaction of the antrum growth factor activity with other cytokines, its activity was tested to determine if it was additive with EGF in epithelial cell cultures. EGF (50 ng/ml) added with untreated mouse antrum extract (10 μg/ml), or heated, dialyzed pig extract (10 μg/ml) exhibited additive stimulation of mitogenesis; up to 74% increase in cell number above the quiescent level; the greatest stimulation observed so far for any factor using the BSC-1 cell assay. An example of this additivity is shown for an AMP-peptide and EGF on AGS cells in FIG. 11. This observation suggests that AMP-18 and EGF initiate proliferation by acting on different cell surface receptors. It also implies that AMP-18 growth factor activity might normally collaborate with other autocrine and paracrine factors in the maintenance or restitution of the epithelium. In view of the results with EGF, it is likely that AMP-18 is secreted at and acts upon the apical face (i.e., stomach lumenal face) of the epithelial cell layer while other factors (for which EGF may serve as an example) act from the basal surface.

11. Bioactivity of Gastrokine (AMP-18) Related Peptides.

The activities of synthetic peptides of the present invention are unexpected. Peptides based on the ORF of the human cDNA clone peptides were synthesized in the University of Chicago Cancer Center Peptide Core Facility, which checks the sequence and mass spectra of the products. The peptides were further purified by HPLC. Five relatively large oligopeptides (of about 40 amino acids each) approximately spanning the length of the protein without including the signal peptide, were analyzed. One peptide 42 amino acids long spanning amino acids lys-78 to leu-119 of the pre-AMP sequence (peptide 58-99 of the matured form of the protein; see Table 1), including a predicted helix and glycine-proline (GP) turns, gave good mitogenic activity. This response was blocked by the specific antiserum, but not by the preimmune sera.

TABLE 1

BIOACTIVITY OF SYNTHETIC PEPTIDES BASED ON THE SEQUENCE OF PRE-GASTROKINE (PRE-AMP-18)

| Name of Peptide Sequence in Human | # AA | AMINO ACID SEQUENCE | $K_{1/2}$, μM |
|---|---|---|---|
| 78-119 | 42 | KKTCIVHKMKKEVMPSIQSLDALVKE**KKLQGKGPGGPPPK**GL (SEQ ID NO: 17) | 0.3 |
| 78-88 | 11 | KKTCIVHKMKK (SEQ ID NO: 14) | Inactive |
| 87-105 | 19 | KKEVMPSIQSLDALVKEKK (SEQ ID NO: 15) | Inactive |
| 104-117 | 14 | **KKLQGKGPGGPPPK** (SEQ ID NO: 11) | 0.8 |
| 104-111 | 18 | **KKLQGKGPGGPPPK**GLMY (SEQ ID NO: 18) | 1.0 |
| 97-117 | 21 | LDALVKE**KKLQGKGPGGPPPK** (SEQ ID NO: 12) | 0.3 |
| 97-117** | 21 | GKPLGQPGKVPKLDGKEPLAK (SEQ ID NO: 19) | Inactive |
| 97-121 | 25 | LDALVKE**KKLQGKGPGGPPPK**GLMY (SEQ ID NO: 13) | 0.2 |
| 109-117 | 9 | KGPGGPPPK (SEQ ID NO: 20) | 2.5 |
| 104-109 | 6 | KKLQGK (SEQ ID NO: 21) | 7.4 |
| 110-113 | 4 | GPGG (SEQ ID NO: 22) | Inactive |
| mouse | | | |
| 97-119 | 23 | LDTMVKEQK . . . GKGPGGAPPKDLMY (SEQ ID NO: 23) | 0.2 |

**scrambled

Table 1: Analysis of mitogenic peptides derived from the human and mouse pre-gastrokine (pre-AMP-18) sequence. A 14 amino acid mitogenic domain is in bold type. *Peptides are identified by their position in the amino acid sequence of the pre-gastrokine (preAMP-18). #AA; number of amino acids in a peptide. $K_{1/2}$; concentration for half-maximal growth stimulation.

Overlapping inactive peptides can inhibit the activity of the mitogenic peptides: that is, human peptides 78-88 and 87-105 block the activity of peptide 78-119, and while peptide 87-105 blocks the activity of peptide 104-117, the peptide 78-88 does not. Peptides 78-88 and 87-105 block the activity of the protein in stomach extracts.

12. The Growth Stimulatory Domain of Gastrokine (AMP-18).

Finding that a 42-amino acid peptide representing a central region of the novel antrum mucosal cell protein AMP-18 had mitogenic activity similar in character to that of the intact protein in pig and mouse antrum extracts (Table 1), has facilitated the characterization of the bio-active region of the molecule. A peptide including amino acids at positions 78-119, gave similar maximal stimulation of growth of the BSC-1 epithelial cell line to that given by the tissue extracts and was similarly inhibited by several different antisera raised in rabbits to the bacterially-expressed complete antrum protein. The mitogenic activity of a number of synthetic "deletion" peptides related to peptide "78-119" are summarized in Table 1. Growth activity determinations have so far been accomplished with the kidney epithelial cell line as well as several gastric and intestinal lines.

The original 42 amino acid sequence of peptide 78-119 was broken into three segments bounded by lysine (K) residues; N-terminal to C-terminal these are peptides with amino acids at positions 78-88, 87-105 and 104-117. Of these only peptide 104-117 possessed mitogenic activity giving a similar plateau of growth stimulation but requiring a higher molar concentration than the original peptide "78-119"; this is reflected in the higher $K_{1/2}$ value, which suggests that 14-amino acid peptide has 30-40% of the activity of the 42-amino acid peptide. A conclusion from this is that the smaller peptide has less binding affinity for a cell receptor, perhaps due to a lessened ability to form the correct conformation, or alternatively because of the loss of ancillary binding regions. The latter notion is supported by the observations that peptides "78-88" and "87-105" can antagonize the activity of intact 42-mer peptide 78-119; these peptides also antagonize the activity of antrum extracts further supporting the validity of synthetic peptides as a means to analyze the biological function of the novel protein. An additional aspect of the invention is that peptide 87-105, but NOT 68-88, antagonizes the activity of peptide 104-117; note that peptide 87-105 overlaps the adjacent 104-117 sequence by two residues.

Taken together these results suggest a relatively simple linear model for the growth-stimulatory region of AMP-18; viz, there is an N-terminal extended binding domain (predicted to be largely helix, the relative rigidity of which may explain the linear organization of the relevant sequences as determined in the cell growth studies), followed by a region high in glycine and proline with no predicted structure beyond the likelihood of turns. It is this latter region which contains the trigger for growth stimulation. The specificity of antagonism by peptides 78-88 and 87-105 may be based on whether they overlap or not the agonist peptides 78-119 and 104-117; for example 78-88 overlaps and inhibits 78-119, but does not overlap or inhibit 104-117. The specificity of competition by these peptides taken with the inactivity of the 78-119 scrambled peptide, strengthens a conclusion that AMP-18 interacts with specific cellular components. Further evidence that the receptor binding region extends N-terminally from peptide 104-117 is provided by the enhanced activity of peptide 97-117 which contains a seven amino acid N-terminal extension of 104-117. A peptide with a four amino acid extension in the C-terminal direction (peptide 104-121) appears to have slightly less activity to the parent 104-117, but does include a natural tyrosine, which makes possible labeling with radioactive iodine, which allows determination of the binding of AMP-related peptides to cells, initially by assessment of number of binding sites and subsequently detection of the receptor protein(s).

The peptide 97-107 was used for most tests because of its activity (equal to the 42-mer) and its relative economy (21 amino acids in length). However, a C-terminal extension to the tyr-121 gives the most active peptide thus far, perhaps because it stabilizes secondary structure. Even though this peptide does not match the nanomolar activity of EGF, for example, it is much more potent than reported for trefoil peptides (Podolsky, 1997). An estimate for the activity the intact AMP protein is ca. 1-10 nM.

13. Expression of Recombinant Protein (a) *E. coli*. Recombinant constructs are generally engineered by polymerase-chain-reactions using synthetic oligonucleotides complementary to the appropriate regions of the full-length cDNA sequences within the PT/CEBP vector and extended by convenient restriction enzyme sites to enable ready insertion into standard vector polylinkers. The initial experiments with expression of the AMP ORF in bacterial systems employed an expression vector PT/CEBP, which included an N-terminal His6-tag (SEQ ID NO: 16) (Jeon et al., 1994), intended to facilitate the purification of the expressed protein on Ni-NTA resin (Qiagen). Expression of the full-length human cDNA within this vector in the host BL21 (DE3)pLyS gave good yields of insoluble protein, which after electrophoresis under denaturing conditions was suitable for use as an immunogen in rabbits to obtain specific high-titer antibodies, but which has not been useful for analysis of the protein's native structure and function. This insolubility is most probably due to the presence of an unnatural N-terminus, having a His6-tag (SEQ ID NO: 16) upstream of hydrophobic signal peptide, in the expressed protein. Engineering vectors which will express the ORF without the hydrophobic signal peptide sequence are also useful. These are constructed using bacterial expression vectors with and without N- or C-terminal His-tags. The human AMP-18 sequence lacking the 20 amino acid signal peptide and containing a His6-tag (SEQ ID NO: 16) was also expressed in bacteria.

(b) *Pichia pastoris*. Among the simple eukaryotes, the budding yeast *P. pastoris* is gaining wide popularity as an expression system of choice for production and secretion of functional recombinant proteins (Romanos et al., 1992; Cregg et al., 1993). In this system, secretion of the foreign protein may utilize either its own signal peptide or the highly compatible yeast mating-type alpha signal. This organism will correctly process and secrete and at least partially modify the AMP-18 protein. Vectors for constitutive and regulated expression of foreign genes are developed in *Pichia* (Sears et al., 1998). In addition to a poly-linker cloning site, these vectors contain either the high expression constitutive glyceraldehyde-3-phosphate dehydrogenase (GAP) or the methanol-regulated alcohol oxidase promoter (AOX1). The latter is an extremely stringent promoter yielding insignificant product in normal culture conditions while giving the highest expression of the vectors tested in the presence of methanol, amounting to as much as 30% of the cell protein. The advantage that the yeast *Pichia* has over the mammalian and insect alternatives is that it is continuously grown in protein-free media, thus simplifying the purification of the expressed protein and eliminating extraneous bioactivities originating in the serum or the host animal cells. A pIB4 construct (inducible by methanol-containing medium) contains the complete human preAMP-18 cDNA sequence.

(c) Baculovirus/Insect cells. An alternative, frequently successful, non-mammalian eukaryotic expression system is that using recombinant Baculovirus, such as *Autographa californica*, in an insect cell culture system. As with *Pichia*, a large repertoire of convenient vectors are available in this system, containing both glutathione S-transferase (GST)-and His6-tags (SEQ ID NO: 16) (Pharmingen). Transfections are carried out into *Spodoptera frugiperda* (Sf) cells; these cells can be slowly adapted to protein-free medium to favor the purification of secreted proteins. If an endogenous signal peptide does not function in these cells, secretion of foreign proteins can also be forced using vectors containing the viral gp67 secretion signal upstream of the cloning site. Recombinant proteins can be expressed at levels ranging from 0.1-50% total cell protein. Some protein modifications may be more favored in this insect cell system relative to yeast, but still may not duplicate the mammalian system. It appears that the insect expression system would be somewhat more onerous than *Pichia*, and not entirely substitute for expression in mammalian cells. The human AMP-18 sequence lacking the 20 amino acid signal peptide and containing a His6-tag (SEQ ID NO: 16) was expressed in Baculovirus.

(d) Mammalian cells. Modifications not detectable by immunoblot analysis may take place in mammalian cells that are not duplicated in cells of other eukaryotes. Although not as convenient as prokaryotic and simple eukaryotic systems, mammalian cells are now frequently used for both transient and continuous expression of foreign proteins. Several growth factors have been expressed and secreted in significant amounts using these systems.

The plasmid pcDNA3/human kidney 293 system: pcDNA3 contains a polylinker cloning site flanked by the strong constitutive cytomegalovirus (CMV) promoter and a SV40 polyA signal (Invitrogen). Laboratory experience is that 60-90% transient transfection levels can be achieved. To this end, PCR amplification of the human preAMP cDNA clone is performed with oligonucleotides that contain the initiation codon and native ribosome binding site (Kozak sequence) as well as suitable restriction enzyme linkers for correct orientation into pcDNA3. Favorable constructs were identified in the transient assay using the potent antibiotic blasticidin S and a vector containing the resistance gene, stable mammalian transfectant cell lines can be established "in less than one week" (Invitrogen). The available vectors also include the constitutive CMV promoter, a polylinker cloning site, an elective V5-epitope/His6-tag (SEQ ID NO: 16) and the SV40 poly(A) signal (PcDNA6/V5-His).

14. Expression and Analysis of Altered (Modified) Forms of AMP-18 Given an efficient expression system for the production of "wild-type" AMP-18, a series of mutant proteins, containing either deletions or substitutions may be created, which will permit analysis of the functional domains. The amphipathic helices, the conserved cystine (C) residues and the basic amino acids doublets, which may be cleavage sites, are attractive targets. Although not as simple as an enzyme assay, the mitogenesis assay is routine and replicable, and would enable "mutants" to be characterized as fast as they are constructed. Dominant negative (or positive) "mutants" will be as significant as mutations exhibiting simple loss of function, because these will imply interactions with other factors including possible cell receptors.

15. Biochemical and Immunoaffinity Fractionation of Expressed and Native Gastrokine Proteins In the case of some of the expressed forms of gastrokine AMP-18, the recombinant protein will contain peptide tags that will permit the rapid purification of soluble protein. The presence of these tags, if they do not severely interfere with the protein's normal functions, will also permit analysis of interactions with other relevant macromolecules. His6-tags (SEQ ID NO: 16) permit purification by binding the recombinant proteins to Ni—NTA resin beads (Janknecht et al., 1991; Ni—NTA resin from Qiagen). The tagged protein is bound with greater affinity than most antigen-antibody complexes and can be washed rigorously before the $N_i^{2+}$-histidine chelation complex is disrupted by excess imidazole to release the purified protein. GST-tagged recombinant proteins are purified on glutathione-agarose, washed and then eluted with reduced glutathione (Smith and Johnson, 1988). As with all the proposed expression systems, each protein preparation may be tested at the earliest possible stage for its growth factor activity.

Conventional fractionation procedures are used to achieve the desired purity, particularly in the case of the isolation of the natural protein from tissue. Pig antrum mucosa is a preferred starting point for the latter, using initial centrifugation and heat-treatment protocol, followed by a size-exclusion column: BioGel P60 is suitable, given the evidence that the 18 kDa protein exists, most probably as a monomer in the extracts. The eluant is loaded on an immunoaffinity matrix created by crosslinking anti-AMP antibodies purified on HiTrap Protein A to CNBr-activated Sepharose 4B (Pharmacia). Further modification of the immunoaffinity matrix may be helpful, either by extension of the linker to the matrix, which has proven useful in the past (Aithal et al., 1994), or by crosslinking the antibody to immobilized protein-A. Because active protein can be recovered by SDS-gel elution, active protein may also be recovered from the antigen-antibody complexes. Further fractionation could be achieved by C8 reversed-phase high-performance liquid chromatography (HPLC) column. A final step is the use of the SDS-gel elution technique with confirmation of identity by N-terminal sequencing. In all of these steps the immunodetectable AMP-18 and the growth factor activity should fractionate together.

16. AMP-18 Related Synthetic Peptides

AMP-18 may be precursor to one or several bioactive peptides. Synthetic peptides provide a convenient avenue to explore the function of a protein; peptides may mimic aspects of the function or antagonize them. If a peptide either duplicates or inhibits the protein's activity, then it suggests the identity of functional domains of the intact protein, and also provides the possibility of synthesizing specifically tagged probes to explore protein-cell interactions.

Finding that a synthetic 42 amino acid peptide, representing a middle region of the human protein, is capable of mimicking the growth factor activity of the partially fractionated antrum mucosal extracts has provided a short-cut to the analysis of AMP-18 function. This peptide (designated peptide 58-99; amino acids are at positions 58-99 of the mature protein after removal of the signal peptide) in addition to several possible protein processing sites at lysine pairs, contains one of the regions capable of extended helix formation as well as a glycine-proline loop. An added advantage of this peptide is that it contains epitopes recognized by both of the antisera disclosed herein. Some smaller peptides derived from this sequence were synthesized to focus on the bioactive regions. Initially sequences bounded by the lysine residues were studied because they may indicate distinct domains within the protein structure, by virtue of being exposed on the surface of the protein, as witnessed by the antigenicity of this region, and may be sites of cleavage in vivo to bioactive peptides. The glycine-proline region is important (see Table 1 illustrating the bioactive domains of AMP-18). Glycine-proline sequences are known to be involved in SH3 (src homology domain type 3) ligands (see Cohen et al., 1995; Nguyen et al., 1998); because SH domains are involved in protein-protein interactions that GP region of AMP-18 may be involved in the interaction of the protein with a cell surface receptor. The exact GPGGPPP (SEQ ID NO: 24) sequence found in AMP-18 has not been reported for the intracellular-acting SH3 domains, so the intriguing possibility exists that it represents a novel protein interaction domain for extracellular ligands. A 21-mer derived from amino acids at positions 97-117 of the mature sequence has activity similar to the 42-mer. This shorter peptide is useful for growth assays on various epithelial cell lines. This peptide does not express the epitope recognized by the antisera disclosed herein.

All of the AMP-18 derived peptides were synthesized by the Cancer Center Peptide Core Facility of the University of Chicago, which also confirmed the molecular mass and amino acid sequence of the purified peptides that are isolated by HPLC. The biological activity of peptide 78-119 not only provides the basis for seeking smaller peptides with mitogenic activity, but permits amino acid substitutions that have positive or negative effects to be found rapidly. Inactive peptides were tested for their ability to block the function of active peptides or intact AMP-18. The possible inclusion of D-amino acids in the peptides (in normal or reverse order) may stabilize them to degradation while permitting retention of biological function. Further the ability to synthesize active peptides enables tags that facilitate studies of the nature, tissue distribution and number of cellular receptors. Such tags include His-6 biotin or iodinated tyrosine residues appended to the peptide sequence (several of the bioactive peptides have a naturally occurring tyrosine at the C-terminus).

Synthetic peptides also permit assessment of the role of potential secondary structure on function. The finding that a 4 amino acid C-terminal extension of the active peptide 97-117, predicted to promote a helix similar to that for the intact AMP-18 sequence, led to a more active peptide 97-121, is interesting. The helix-propensity of these active peptides e.g. peptide 126-143, which resembles an anti-microbial magainin peptide, provides useful information. With respect to anti-microbial peptides, the function of the magain in class is related to their ability to form amphipathic helices (Boman, 1995). Synthetic peptides that can be locked in the helical form by lactam bridges (Houston et al., 1996) enhanced biological activity; at least one pair of appropriate acidic and basic amino acid residues for lactam formation already exist in potential helix regions of AMP-18.

Another equally significant aspect of the peptide studies is the potential availability of specific anti-AMP-18 peptides that antagonize its biological functions. Tissue culture studies show that sub-peptides of the growth-promoting peptide 78-119 can antagonize the activity of the intact peptide (see Table 1). Peptides that can occupy cellular binding sites but lack some essential residues for activity may block the action of AMP-18 and its active peptides. This makes available another set of reagents for the analysis of cellular receptors and for assessing receptor-ligand affinity constants. Availability of defined peptide antagonists is useful in whole animal studies, and may eventually serve to regulate the activity of the natural protein in humans.

17. Interactions of AMP-18 and Related Peptides with Cells: Assessment of Cell Growth Non-transformed monkey kidney epithelial cell line BSC-1 and other epithelial cell lines were used to assess effects on growth. In general, conditions were chosen for each line such that cells are grown to confluence in plastic dishes in supplemented growth medium with minimal calf (or fetal) serum for growth (Lieske et al., 1997); BSC-1 cells become confluent at $10^6$/60 mm dish with 1% calf serum. At the start of the growth assay the medium on the confluent culture was aspirated and replaced with fresh medium with minimal serum to maintain viability (0.01% for BSC-1) cells. AMP-18 preparations were added to the culture medium and 4 days later the cell monolayer was rinsed, detached with trypsin, and the cells were counted using a hemocytometer. Determination of the capacity of AMP-18 to initiate DNA synthesis was measured by the incorporation of [$^3$H]thymidine (Toback, 1980); to confirm the DNA synthesis assay, autoradiograms of leveled cells were counted (Kartha and Toback, 1985).

The protein AMP-18 is expressed in the antrum mucosa and to a lesser extent in the adjacent corpus mucosa. However, both antrum extracts and the active synthetic peptides stimulate proliferation of most simple epithelial cell lines. The major criterion used, apart from cells which might be natural targets for AMP-18 or its peptides, was that of growth control, particularly cell-density restriction. Many transformed stomach lines derived from human cancer patients are available from various sources, but most of these do not exhibit growth control. For example, a gastric AGS adenocarcinoma cell subline from Dr. Duane Smoot (Howard University College of Medicine) showed a greater degree of contact inhibition, and responded well to AMP-18 and its derived peptides. These cells do not naturally synthesize AMP-18. Similar responses were observed with the non-transformed rat IEC intestinal epithelial cells (provided by Dr. Mark Musch, Dept. Medicine, University of Chicago); the latter show excellent epithelial cell characteristics in culture (Quaroni et al., 1979; Digass et al., 1998).

18. Receptors for AMP-18 on the Surface of Epithelial Cells

Characterization of the target cell receptors of AMP-18 is intriguing because of the apparent existence of receptors on cells which are not expected ever to contact this protein. Initial growth response assays were performed on kidney-derived epithelial cell lines, which responded well to the stomach factor. Gastric cell lines, as well as the non-transformed rat intestinal epithelial IEC-6 cells, were used to address the receptors in cells that are likely the true physiological targets for the antrum factor. The specificity for the action of this protein in vivo likely arises from the extremely tissue specific nature of its expression, rather than that of its receptor. It is possible that AMP-18 may interact with receptors shared with other growth factors.

However, the additive growth stimulus of EGF and the antrum extracts suggest that AMP-18 may have novel receptors. Protein molecules in cell membranes that interact with AMP-18 may be sought in several different ways. Pure AMP-18 or related peptides labeled, e.g. with biotin or radioactive iodine, are used to estimate the number of saturatable sites on the cell surface. Scatchard analysis of the binding values as used to determine the number and affinity of receptors. For quantitative studies, binding is measured at increasing AMP ligand concentrations, and non-specific components are identified by measuring binding in the presence of excess unlabeled factor. Iodinated growth factors have been cross-linked to cellular receptors enabling their identification (Segarini et al., 1987). Labeled AMP ligands are incubated with cells, and the bound ligand is cross-linked to the receptors by disuccinimidyl suberate. The labeled proteins are resolved by SDS-PAGE, and autodiography is used to visualize the cross-linked complex permitting an estimate of the MW of the receptor(s). Synthetic peptide mimics or antagonists permit studies of the cellular receptors, and their properties are reasonably inferred prior to future definitive identification, presumably by cloning techniques.

In addition to crosslinking studies, antibodies, or his6-tagged (SEQ ID NO: 16) AMP-18 or peptides are used to isolate cellular or mucus proteins which bind to AMP-18. As an additional approach, an immobilized AMP-18 affinity matrix can be created by using CNMBr-activated Sepharose. As a simple beginning to the analysis of the signal transduction pathway mediated by any cell receptor, a test to assay protein tyrosine kinase activity in affinity isolates is available (Yarden and Ullrich, 1988; Schlessinger and Ullrich, 1992).

19. Is AMP-18 Processed to Bioactive Peptides?

The functional molecular form(s) of AMP-18 is not known. Certainly, the ca. 18 kDa is the protein form which accumulates in antrum mucosal cells, and substantial amounts of polypeptides of lower MW are not detected with the antisera, even though they do react with pepsin fragments down to ca. 10 kDa and also with the bioactive peptide 78-119 (having only 42 amino acids). Having access to labeled or tagged AMP-18 enables a question of whether the protein is processed in antrum mucosal extracts, or by the epithelial cells which respond to it, to be explored.

20. Genes for AMP-18 in Man and Mouse

Using PCR techniques employing primers based on the sequence of the human cDNA clone, genomic clones of human and mouse preAMP-18 were obtained. The exon/intron structure (FIG. 12) is complete. Mouse AMP exons are sufficiently similar to those of human and pig to allow a sequence of the mouse gene to be assembled. Human and mouse genes have very similar structures, the mouse gene being slightly smaller. The ORF contained in exons of the mouse gene predicts a protein having 65% identity to the human and pig proteins. A 2 kb of sequence is upstream of the human gene.

21. Knockout of the AMP-18 Gene in Mouse

From the mouse map a targeting construct is designed. The construct preferably contains: [5'-TK (a functional thymidine kinase gene)-ca. 5 kb of the 5' end of AMP-18 DNA-the neomycin phosph-transferase (neo) gene under the control of the phosphoglycerate kinase (PGK) promoter -ca. 3 kb of the 3' end of the gene —3']. A considerable length of homology of the construct with the resident AMP-18 gene is required for efficient targeting. Increasing the total homology from 1.7 to 6.8 kb increases the efficiency of homologous targeting into the hrpt gene about 200-fold (Hasty et al., 1991). Beyond that total length, the efficiency increases only slightly. To facilitate the detection of homologous intergrants by a PCR reaction, it is useful to have the neo gene close to one end of the vector. The resulting transfectants can be provided by PCR with two primers, one in the neo gene and the other in the AMP-18 locus just outside of the targeting vector. Flanks extending 4 kb 5' and 4.5 kb 3' of the mouse gene have been obtained. Through homologous recombination, the coding region will be replaced by the neo gene to ensure a complete knockout of the gene are already cloned. After trimming off the plasmid sequence, the targeting cassette will be transfected into ES cells and stable transfectants obtained by selection with G418, an analog of neomycin, and gancyclovir (Mansour et al., 1988). Southern blots with the probe from the flanking sequence will be used to screen for targeted homologous recombinants. Correctly targeted ES cell clones will be injected in blastocysts from C57BL/6 mice.

Male offspring obtained from surrogate mothers that have at least 50% agouti coat (embryonic stem cell (ES) cell derived) are bred with C57BL/6 mice. F1 mice that are agouti have the paternal component derived from the ES cells (agouti is dominant over black). 50% of these mice should have the knockout preAMP-18 allele. These hemizygous mice are monitored for any effect of diminished gene dosage. Homozygous knockouts are preferable. If the sole function of AMP-18 is in the stomach following birth, then viable homozygotes are expected. If these cannot be obtained, a fetally lethal defect would be indicated, and the fetal stage of abortion would be ascertained. This result would suggest an unanticipated role of the protein in normal development.

Homozygous AMP-18 knockout mice are useful for investigations of stomach morphology and function. It is expected that such knockouts will show if AMP-18 is essential, and at which stage of gastro-intestinal development it is bioactive. It is possible that the AMP-18 knockout hemizygous mice will already show a phenotype. This could occur if reduced dosage of the protein reduces or eliminates its function, or if parental imprinting or random mono-allelic expression has a significant influence. A range of possible outcomes of the AMP-18 knockout in mice include: i) no viable homozygotes, implying an essential unanticipated developmental role; ii) viable homozygotes, but with obviously impaired gastrointestinal functions; iii) no strong phenotype, i.e. the protein is not important to the development and life of the laboratory mouse. If appropriate, the generation of AMP-18 in overexpressing mice is pursued. A truncated AMP-18 protein produced in the mice could potentially create a dominant negative phenotype; knowledge gained from the experiments will further define the functional domains of the protein.

Abbreviations for amino acids

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

DOCUMENTS CITED

Aithal, N. H., et al. (1994) *Am. J. Physiol.* 266:F612-619.

Altschul, S., (1997) et al. (1994) *Nuc. Acids Res.* 25:3389-3402.

Baczako, K, et al. (1995) *J. Pathol.* 176:77-86.

Blaser, M. J. et al. (1987) *Gastroenterol.* 93:371-383
Boman, H. G. (1995) *Ann. Rev. Immunol.* 13:61-92.
Cohen, G. B., et al. (1995) *Cell* 80:237-248.
Cregg, J. M., et al. (1993) *Bio/Technol.* 11:905-910.
Dignass, A. U., et al. (1998) *Eur. J. clin. Invest.* 28:554-561
Falk, P., et al. (1993) *Proc. Nat. Acad. Sci.* 90:2035-2039.
Goodwin, C. S., et al., (1986) *J. Clin. Microbiol.* 39:353-356
Hasty, P., et al. (1991) *Mol. Cell. Biol.* 11:5586-5591.
Houston, M. E., et al. (1996) *Biochem.* 35:10041-10050.
Janknecht, R., et al. (1991) *Proc. Nat. Acad. Sci. USA* 88:8972-8976
Jeon, C. J., et al. (1994) *Proc. Nat. Acad. Sci. USA* 91:9106-9110
Johnson, F. R. and McMinn, R. M. H. (1970) *J Anat.* 107:67-86.
Kartha, S. and Toback, F. G. (1985) *Am. J. Physiol.* 249: F967-F972
Kartha, S., et al. (1992) *Exp. Cell Res.* 200:219-226.
Lacy, E. R. (1998) *J. Clin. Gastroenterol.* 10(Suppl 1):72-77.
Lieske, J. C., et al. (1994) *Proc. Natl. Acad. Sci.* 91:6987-6991.
Lieske, J. C., et al. (1997) *Am. J. Physiol. F*224-F233.
Mansour, S., et al. (1988) *Nature* 336:348.
Moore, K. S., et al. (1991) J. Biol. Chem. 266:19851-19857.
Nguyen, J. T., et al. (1998) *Science* 282:2088-2092.
Nomura, A., et al. (1991) *N. engl. J. Med.* 325-1132-1136.
Nusrat, A., et al. (1992) J. Clin. Invest. 89:1501-1511.
Park, C. B., et al. (1997) *FEBS Lett.* 411:173-178.
Parsonnet, J., et al. (1991) *N. Engl. J. Med.* 325:1127-1131.
Podolsky, D. K. (1997) *J Gastroenterol.* 32:122-126.
Powell, C. J., (1987) *Ph.D. Dissertation, University of Chicago.*
Quaroni, A., et al. (1979) *J. Cell Biol.* 80:248-265.
Romanos, M. A., et al. (1992) *Yeast* 8:423-488.
Rotimi, V. O., et al. (1990) *Afr. J. Med. med. Sci.* 19:275-280.
Sands, B. E. and Podolsky, D. K. (1996) Ann. Rev. Physiol. 58:253.
Schiessinger, J. and Ullrich, A. (1992) *Neuron* 9:383-391.
Sears, I. B., et al. (1998) *Yeast* 14.
Segarini, P. R., et al. (1987) *J. Biol. Chem.* 262:14655-14662.
Smith, D. B. and Johnson, K. S. (1988) *Gene* 67:31-40.
Toback, F. G. (1980) *Proc. Nat. Acad. Sci.* 77:6654-6656.
Yarden et al. and Ullrich (1988) *Biochemistry* 27:3113-3119.
Yoo, O. J. et al. (1982) *PNAS* 79:1049-1053.
Yoshikawa, Y., et al. (2000) *Jap. J, Cancer Res.* 91:459-463.

We claim:

1. A method to stimulate growth of epithelial cells in the gastrointestinal tract of mammals, said method comprising:

(a) contacting the epithelial cells with a composition selected from the group consisting of a protein comprising SEQ ID NO:3, a peptide comprising amino acid positions 21-185 of SEQ ID NO: 3, a peptide comprising amino acid positions 78-119 of SEQ ID NO: 3, a peptide comprising amino acid positions 97-117 of SEQ ID NO: 3, a peptide comprising amino acid positions 97-121 of SEQ ID NO: 3, and a peptide comprising amino acid positions 104-117 of SEQ ID NO: 3, and (b) providing environmental conditions for stimulating growth of the epithelial cells.

* * * * *

```
                        SEQUENCE LISTING

<160> NUMBER OF SEQ ID NOS: 26

<210> SEQ ID NO 1
<211> LENGTH: 7995
<212> TYPE: DNA
<213> ORGANISM: Homo sapiens

<400> SEQUENCE: 1

agctttataa ccatgtgatc ccatcttatg gtttcaatcc atgcacagga ggaaaattgt      60

gggcacgaag tttccaaagg gaaaatttat agattggtag ttaatgaaat acagttttcc     120

tccttggcaa atttaattta ctagcttcac tgtataggaa aaagcaggaa aaaaattaaa     180

accaactcac ctccaaacct gttttgagct tttacttgtc tgcccaattg atagtttcta     240

ctctctgctt ttgatgaaaa tattttttat tattttaatg taacttctga aaactaaatt     300

atctagaagc aaataaaaag atattgcttt tatagttccc agaaggaaaa aacaaacact     360

aggaaagttc tatctatcag atgggggaga tgtgatggag gcagtgatat ttgagctgag     420

ccttgaacaa tgaacaggag tctaccaagc gagaggctag cgggtggccc tcaagataaa     480

acaacagcat gtacaaaggc atggagacat acacatcttg actcttccag gaatggtggg     540

aacgctggtg gagctagaat gtaggtacat agcataaagt ggcagacggg aagcctttgg     600

aaatcttatt acataggacc ctggatgcca ttccaatgac tttgaatttt ctgtaggctg     660

ccagcgaaat ttccaagcgt gatagagtca tgtctatcta tgcacttcag aaagacaacc     720

tcagggttaa tgaagaaaat gcattggaat ataagaaact ggtgaccaga gtgatcaatt     780

gcatgactgt tgtgaaagtc caggtgaggg gagctgtggg caaggtcaga gttgagaggc     840

atttcagaga taaaatgaca gtaactaagt agatgtcagg ctgagaagaa agggctgtac     900

cagatatatg gtgctatcat taagtgagct caacattgca gaaaaggggt aggtttggtg     960

ggagttgctc acaaaacatg tttagtctaa gcaaaaccat tgccatgggc tcagataaaa    1020

gttaagaagt ggaaaccatt cctacattcc tataggagct gctatctgga aggcctagta    1080

tacacgtggc ttttcagctg tgattttgtt tgattttagg gattattctt tttctgaatc    1140
```

-continued

```
tgagcaatgt tagcgtgtaa aatactcaca cccacagctt tgactgggtg agaagttatc   1200
ataaatcata ttgagtttgt tgtgatacct tcagcttcaa caagtgatga gtcaggtcaa   1260
ctccatgtga aagttccttg ctaagcatgc agatattctg aaaggtttcc tggtacactg   1320
gctcatggca cagataggag aaattgagga aggtaagtct ttgaccccac ctgataacac   1380
ctagtttgag tcaacctggt taagtacaaa tatgagaagg cttctcattc aggtccatgc   1440
ttgcctactc ctctgtccac tgctttcgtg aagacaagat gaagttcaca gtgagtagat   1500
ttttcctttt gaatttacca ccaaatgatt ggagactgtc aatattctga gatttaggag   1560
gtttgcttct tatggcccca tcatggaaag tttgttttaa aaaaattctc tcttcaaaca   1620
catggacaca gagaggggaa caacacacac caggtcctgt tggggggtgg agagtgaggg   1680
gagggaactt agaggacagg tcaatagggg cagcaaacca ccatggcaca catataccta   1740
tgtaacaaac ctgcacgttc tgcacatgta tccctttttt ttagaagaag aaataatgaa   1800
aaaaaacctt ttttctattt atataatcat ggcatttata agcatctcta tagagaagga   1860
taattgtgct gagattagac agctgtctga gcacctcaca ctgacctatt tttaacaaaa   1920
tgactttcca catcacctga tttcggctcc atgcrgggta agcagttcct aagccctaga   1980
aagtgccgat catccctcat tcttgaattc ctccttttat ttaccaaaat tcctgagcat   2040
gttcaggaaa gatgaaaagc ttattatcaa aataagtggc tgagatagac ttcttgtcac   2100
atttgttaca gtaaaatggg tctccaagaa agaaagattt gccttgggct ctagcatggc   2160
catttattta agaaagcatc tgaaacatga agctaccaca gcatctctcc tgtggttcca   2220
gacggaagcc tgagagtcta ggaggaggtg gaccgagaaa ccctgccaaa gtaactagta   2280
gtgccgggtt tctcacaaca cgatgcaaag gggctagaat cagatgacta ttttcatgtt   2340
tcaacatact acacactgga aaacgttacg gcagactcta ctttataatg gggctgcaaa   2400
tgtaaaatga ctactagaac taggtcctct taatagcagc aaagtttaaa agggtcagag   2460
ggagctccag acacaggtta gatttgattt ctctcctagt tctgctgtga acaagaggta   2520
taagtttggc caactcactt aacccctgaa gctcagttac cttatctgta aaatgattgc   2580
attgtactag gtgttctcta aaatttcttc tacctctgac tttttaggag actaattttt   2640
aactcctttt taagctattg ggagaaaaat ttaatttttt ttcaaaagtt accttgaatc   2700
tctagagcag ttctcaaaac tattttgtcc caggcaaagg aaatgagact aggtacccag   2760
aatgaggcac cctgcataaa gctctgtgct ctgaaaacca atgtcaggga ccctgtgata   2820
aataattaaa ccaagtatcc tgggacactg ctagtgacat cgcctctgct gatcactctt   2880
gccagcgaga cactctatac ttgctttctc atcattggca tccaaactgc ctactaatcc   2940
attgctttgg aaagtttttt ttaataaaaa gattatttct attaggagga aaacatccca   3000
tgttaaatag gaaaattaac tgaaatcatt ttcagatgtg atttttagca cttatagcca   3060
tttcaaacca tggtattcat ttatactatg ctatttattg taaaacttct ttttttttcc   3120
aaggaaaata agatagtttg ctttatttta aaacagtaac tttcttatat tggggcactg   3180
accaaaattc aatactggta caaatatgtt acctaggggg tcaaaatatg tgccaggtga   3240
attttctgaa tttctctaaa gagagaattt taaaccttat aaaacaatta gaaacaagtg   3300
agtgagaggt gagcatcaac aacctgtgta acataagcca cagtacaaat ttaagctgaa   3360
taaccaagcc atgtcagtta tcccaaatca tttttgttaa tatttaggag gatacacata   3420
ttttcaataa cttaaaagtg aatctttact cctatctctt aatactcgaa gaagtataac   3480
```

-continued

```
tttcttcttt tactagattt aaataatcca aatatctact caaggtagga tgctgtcatt   3540
aactatagct gagtttatcc aaaatagaaa aatcatgaag atttataaag cattttaaaa   3600
ataatcattt atagcaagtc cttgaaagct ctaaataaga aaggcagttc tctactttct   3660
aataacacct atggtttata ttacataata taattcaaca aaacagcatt ctgaccaatg   3720
ataatttata ggaaattcat ttgccaagta tatgttttat tataaagtta atattttgac   3780
caatcttaaa aatttttaaa ctctattctg acatttccag aagtattatc ttagcaagtc   3840
atctttatga taccacttat taaactgaag agaaacaaga tggtacattc tgggttttac   3900
tttaaaaggg atttgattca ataatttgat ttatcactac ttgaaaatta cattttcttc   3960
ctcagactgg atggcaatga gatgaaagca gctttcctgg ctctcaactt cccttcttca   4020
tcaatttttc cagcgtttca taaggcctac actaaaaatt ctaaaactat atatcacatt   4080
aatataatta cttataatta atcagcaatt tcacattatc gttaaaacct ttatggttaa   4140
aaaatgcaag gtaagagaag aaaaaaacac attgaactag aactgaacac attggtaaaa   4200
ttagtgaata cttttcataa gcttggatag aggaagaaag aagacatcat tttgccatgt   4260
aacaggagac caatgttatt tgtgatttca gattgtcttt gctggacttc ttggagtctt   4320
tctagctcct gccctagcta actatgtaag tctcaccttt tcaagtttgc taccaaaatg   4380
catttgcaag gaaatgtgat attaaatcac tctcaatctc ttataaactt cagaatatca   4440
acgtcaatga tgacaacaac aatgctggaa gtgggcagca gtcagtgagt gtcaacaatg   4500
aacacaatgt ggccaatgtt gacaataaca acggatggga ctcctggaat tccatctggg   4560
attatggaaa tgtaggtagt caacgtgcaa ttttcacttt attgtttaaa aatacgactt   4620
ctttttaaca aaaaatgtgc atgttaacca taaagaaatt aaaaataaat tctaattaca   4680
catagcatac agttataagt aaaggtgacc attttgctca tccgattttg ttccctagag   4740
ataactactg ttaataagtg ttgcatgatc agttaaaatt caaaccaaca aacactatgt   4800
tcaagggatt gtgggtatat acaacaaata tgaacatcct tttgccttgc ctgcagatac   4860
cctcaataat gctgaaagac ttatacaaca ttactgcttc caaagcttag actatctcac   4920
tttgttttca aaggaggttt tacgaccttc taaagagatt gaaattgaca tttcacctaa   4980
aactcgggaa atgtaaatga caatattaat tggtaagaga ggaaagaaga aagaaagaag   5040
gaaggaaaga aagaaagaag gaaggaagga aagaaagaaa gaaagaaaga aagagagaga   5100
aagaaagaaa aagaaaaaag agagaaagag agaaggaaag aaagagagaa ggaaaggaaa   5160
agagaagcaa agaaagagag gagcaaagaa aggaacactt agcactagtt gggagaccca   5220
actctggaat tatcagctat atatttaaca aacgttatac ttttaaatag caaactcttt   5280
attgtttcaa ttttatctgg tcaattggaa aaataatttt tgtcttatct gtctccttga   5340
aatgtgagga tcaaaggaga ctaaaacatg atagctttta aagtctattt cagtaaaaca   5400
gacttatata gaggggtttt tatcatgctg gaacctggaa ataaagcaaa ccagttagat   5460
gctcagtctc tgccctcaca gaattgcagt ctgtccccac aaatgtcagc aatagatatg   5520
attgccaagc agtgccccat ccagtgctct tatcccagct catcacgatc ttggagttcc   5580
catttctctc tgcaggtgga actgacctct gataagaaaa gctcctcgga gaacacatgc   5640
ctcactattt gccatctact ttaacagggc tttgctgcaa ccagactctt tcaaaagaag   5700
acatgcattg tgcacaaaat gaacaaggaa gtcatgccct ccattcaatc ccttgatgca   5760
ctggtcaagg aaaagaaggt aaaaataaaa ggctttttat ttttggtgag gggagaggtt   5820
ttacatcctt cagtaaataa cgagaagatc acagtcattc cctcttgact acagtatgtt   5880
```

-continued

```
gtagtgtgca gcacaaaggg ggaagttatt ggtgattgcc tgagggaagg caacttctgc   5940
cacatcaaat gctgtggctc acacctacct ctacaaccgc tgagcaaagc acttgaaacc   6000
ttgactgtta gaggagcaaa gctctggtca caccaatagg agcctcagta ctttgccaag   6060
gacatttttc tgcaagagtt agttagggtt attagattta gcaaatgaaa atagaagata   6120
tccagttagg tttgaatttt aggtaagcag caggtctttt tagtataata tatcctatgc   6180
aatatttggg atatactaaa aaaagatcca ttgttatctg aaattcaaat gtaactgggt   6240
attgtatatt ttgtctggcc atactaatcc aggtgagtgg aaagaagaga tccataatgt   6300
tttaaaatat ttgcctgagt tcatattcct ataactgata aatgagtacc tttcattgac   6360
aaggtagaga aaataaataa actgcattct cagaagatga ttattacata gtctaatcca   6420
aggaatctat gatgaccaaa tgaggtccaa gttgcagaat aaattaagcc tcagacttct   6480
gtgtttatga gaagctgagg tttcaaacca ggtaaatccc ttaggacact tagaaatgct   6540
aagatataca gaataagcta gaaatggctc ttcttcatct tgattatgga aaaatttagc   6600
tgagcaacac tcactgttgg cctcgtatac ccctcaagtc aacaaaccac tgggcttggc   6660
attcattctc tcccattctt cctttctacc tctcttttcc acactcagct tcagggtaag   6720
ggaccaggag gaccacctcc caagggcctg atgtactcag tcaacccaaa caaagtcgat   6780
gacctgagca agttcggaaa aaacattgca aacatgtgtc gtgggattcc aacatacatg   6840
gctgaggaga tgcaaggtga gtagcatccc tactgtgcac cccaagttag tgctggtggg   6900
attgtcagac tatcctcgcg cgtgtccata gtgggcacca gtgatgcagg gatggtcatc   6960
aaggccaaca tttgtgcagt gcttgctctg tgccaggtac tgttctatgt gctttaagtg   7020
tgttaactcg gttcttcaca gcaatcttat aggttctatt ttaatcctac tttatggatg   7080
aggaaactga ggtacagaga ggtcacaaaa tccttgcctg ggtcaattcc aagcattttg   7140
gctgtggatt ctgtgctctt aaatattatg gaacactgcc ttttaagtgt gaatcaagag   7200
tagactcaag tcatattcaa aagaatgcat gaatggctaa atgaaagaag aatgctaata   7260
gaatctatta actttctata gctcagacaa tcacttaatt tctggacatt caaagaacag   7320
ctgcacacaa acaaagtgtc tacctaggga cctaacttaa tggcaatttt ccagatctct   7380
gaattgattg atttcatcac aacaagtaga taaaccttga cattagcaca tagctagttt   7440
ggaaacccct actcccccaa tcccctccaa gaaaagagtc cttaaataga cattaatata   7500
ggcttcttct tttctcttta ttagaggcaa gcctgttttt ttactcagga acgtgctaca   7560
cgaccagtgt actatggatt gtggacattt ccttctgtgg agacacggtg gagaactaaa   7620
caattttttta aagccactat ggatttagtc atctgaatat gctgtgcaga aaaaatatgg   7680
gctccagtgg tttttaccat gtcattctga aatttttctc tactagttat gtttgatttc   7740
tttaagtttc aataaaatca tttagcattg aattcagtgt atactcacat ttcttacaat   7800
ttcttatgac ttggaatgca caggatcaaa aatgcaatgt ggtggtggca agttgttgaa   7860
gtgcattaga ctcaactgct agcctatatt caagacctgt ctcctgtaaa gaacccccttc   7920
aggtgcttca gacaccacta accacaaccc tgggaatggt tccaatactc tcctactcct   7980
ctgtccactg cttaa                                                    7995
```

<210> SEQ ID NO 2
<211> LENGTH: 752
<212> TYPE: DNA
<213> ORGANISM: Homo sapiens -continued

<400> SEQUENCE: 2

```
catgcttgcc tactcctctg tccactgctt tcgtgaagac aagatgaagt tcacaattgt      60

ctttgctgga cttcttggag tctttctagc tcctgcccta gctaactata atatcaacgt     120

caatgatgac aacaacaatg ctggaagtgg gcagcagtca gtgagtgtca acaatgaaca     180

caatgtggcc aatgttgaca ataacaacgg atgggactcc tggaattcca tctgggatta     240

tggaaatggc tttgctgcaa ccagactctt tcaaaagaag acatgcattg tgcacaaaat     300

gaacaaggaa gtcatgccct ccattcaatc ccttgatgca ctggtcaagg aaaagaagct     360

tcagggtaag ggaccaggag gaccacctcc caagggcctg atgtactcag tcaacccaaa     420

caaagtcgat gacctgagca agttcggaaa aaacattgca aacatgtgtc gtgggattcc     480

aacatacatg gctgaggaga tgcaagaggc aagcctgttt ttttactcag gaacgtgcta     540

cacgaccagt gtactatgga ttgtggacat ttccttctgt ggagacacgg tggagaacta     600

aacaattttt taaagccact atggatttag tcatctgaat atgctgtgca gaaaaaatat     660

gggctccagt ggtttttacc atgtcattct gaaatttttc tctactagtt atgtttgatt     720

tctttaagtt tcaataaaat catttagcat tg                                   752
```

<210> SEQ ID NO 3
<211> LENGTH: 185
<212> TYPE: PRT
<213> ORGANISM: Homo sapiens

<400> SEQUENCE: 3

```
Met Lys Phe Thr Ile Val Phe Ala Gly Leu Leu Gly Val Phe Leu Ala
  1               5                  10                  15

Pro Ala Leu Ala Asn Tyr Asn Ile Asp Val Asn Asp Asp Asn Asn Asn
             20                  25                  30

Ala Gly Ser Gly Gln Gln Ser Val Ser Val Asn Asn Glu His Asn Val
         35                  40                  45

Ala Asn Val Asp Asn Asn Asn Gly Trp Asp Ser Trp Asn Ser Ile Trp
     50                  55                  60

Asp Tyr Gly Asn Gly Phe Ala Ala Thr Arg Leu Phe Gln Lys Lys Thr
 65                  70                  75                  80

Cys Ile Val His Lys Met Lys Lys Glu Val Met Pro Ser Ile Gln Ser
                 85                  90                  95

Leu Asp Ala Leu Val Lys Glu Lys Lys Leu Gln Gly Lys Gly Pro Gly
            100                 105                 110

Gly Pro Pro Pro Lys Gly Leu Met Tyr Ser Val Asn Pro Asn Lys Val
        115                 120                 125

Asp Asp Leu Ser Lys Phe Gly Lys Asn Ile Ala Asn Met Cys Arg Gly
    130                 135                 140

Ile Pro Thr Tyr Met Ala Glu Glu Met Gln Glu Ala Ser Leu Phe Phe
145                 150                 155                 160

Tyr Ser Gly Thr Cys Tyr Thr Thr Ser Val Leu Trp Ile Val Asp Ile
                165                 170                 175

Ser Phe Cys Gly Asp Thr Val Glu Asn
            180                 185
```

<210> SEQ ID NO 4
<211> LENGTH: 7226
<212> TYPE: DNA
<213> ORGANISM: Mus sp.
<220> FEATURE:
<221> NAME/KEY: modified_base -continued

```
<222> LOCATION: (7030)
<223> OTHER INFORMATION: a, c, t, g, other or unknown
<220> FEATURE:
<221> NAME/KEY: modified_base
<222> LOCATION: (7084)
<223> OTHER INFORMATION: a, c, t, g, other or unknown

<400> SEQUENCE: 4

gaattcaaac agcaggccat ctttcaccag cactatccga atctagccat accagcattc     60

tagaagagat gcaggcagtg agctaagcat cagacccctg cagccctgta agctccagac    120

catggagaag aggaaggttg tgggttcaag gagcttttca gagtggaaat ctgtggatca    180

gtgatttata aaacacagtt tcccccttta ttagatttga accaccagct tcagttgtag    240

aagagaacag gttaaaaaat aataagtgtc agtcagttct ccttcaaaac tattttaaac    300

gtttacttat tttgccaagt gacagtctct gcttcctctc ctaggagaag tcttccctta    360

ttttaatata atatttgaaa gttttcatta tctagagcag tggttctcat cctgtgggcc    420

atgagccctt tggggggtt gaacgaccct ttcacagggg tcacatatca gatatcctgc    480

atcttagcta tttacattat gattcataac agtagcaaaa ttagttagga agtaggaaca    540

aaataacgtt atggttgtgg tcaccactat gttagagggt ccgcagcatt cagagggttg    600

agaactgttg ttctagaggc aaataagaag acagagttcc ttgatagggc ccagaggcag    660

tgaaagaagt ttccacgtag aaagtgaaga aggtctggtg tccgaagcag tgaggaactt    720

aaaaaaagaa aaccaaaaac attgccaact aacagtccag gagaagagcg gggcatgaaa    780

ggctgagttc ccatgggatg ccttgaatgg aatcagagtg tgggaaaatt ggtgtggctg    840

gaaggcaggt gccgggcatc tcagacgctg gtagctgggg aaacaggaaa ccccttttagg    900

atcccaagat gccattccaa tgagcttgag atttttctca tggactgcca gtgaatgttt    960

ctacgctccg gaaattaatg tttacttatt ttccatattc taggggagaa ccctgggaaa   1020

aatggaggac attcattgaa atatctgagt cctgggataa ggcaggcttg gtcctacaac   1080

tctggtaaaa gtccatcagg caaggtttag ttgctagata tgtagatggc aagatggtgc   1140

tgccaacagc ccccagagct ctaacccact gagaaaccca ggaatgaatg atgggagatg   1200

gctttggtgc cagctgctag tgacatggct ggaaagctgc actggcttcg aggccagaca   1260

attcctcaag gaaacatctg gccagggtgc aagggccagt ttccttcctt ggagttcctt   1320

tcacagctaa gaacatcatc ccccaaccac tggttttgtt aaaaagtttt cagtatgact   1380

tgagcatggt caagaagcat agagaggggg aaataagggt ggaaggagct ggagaaagct   1440

tacaatagga ctgggtaaag ggaaggagaa gaaaccattc ccgcattccc ataggagcca   1500

gtaccaggaa gggcaggtgt acacacagat ctcatctaag gccatgtttg gtttagggat   1560

tactcttctc ccgaatctga gcagcagcaa tacgtaaaat acccacaccc atggcttcca   1620

tattccagaa cttatcacaa accgtgtaga gtttactgag ataccttcgt cagaggatga   1680

gtcagaggcc tcctgcctaa gggccctact gagcaggcag ctaaaggctt ccgggcctct   1740

gcagctccac agatacagga gagggaagca gataagccgt ggactccacc tgagcacacc   1800

tagcttgagc aaagctggtc aggtacaaat agcagagggc tgaatgtctg tgagcacgcc   1860

gcctgatcct ctgctccacc acactcctgc cgccatgaag ctcacagtaa gtcagatctt   1920

cttttcaatg cagcaccata caacattaat agtcaggggt gagggggtct gactcttacg   1980

gcactgttac catagtggaa atattctcct ttcttttcat ggaatcatgg tgtttacaag   2040

catgtccata gagaagaaga attgccccgg aagagcctgt cacaggctga atactgtaga   2100
```

-continued

```
attgtctttc acaccatctg ttccaaggtt ctacttaaga cgagcagtct ctgggctcca   2160
gaaagagtct ttcttagcct tgatctcttt cttatttctg atttctcctt tcttatccat   2220
gatttccact tttaccagtt ctgggcatcc ggtcagactg gaagatcact gttgtcaaaa   2280
ctagtcttca acactcttgg ctgttaacat gaaaacaacg gtccttgggc cctgtgcaag   2340
catttcttgg agaaagtctc tggggatgaa gctatctcag tttccccact gaagtcctag   2400
gatacagagg ctcaaacaga gtgcacatat tcaatttcag catactctat tggcgctgct   2460
ttatgaatca tatgaattta tggaattgga aatgtaaact atgaccaaga agcgtccacc   2520
tcagaacagg ttgggtgggg aactccaagc acaggccaga gggctgcgtt tctcttctag   2580
ttctgtctag aggagtggtt ctcgaccttc ctaatgctgt gaccctttaa tacagttcct   2640
cacgttgtcg tgactcccag ccataaaatt actttcattg ctactgcata actgtaattt   2700
tgctaccatt atgagttgta atgtaaatat ctgatatgca agataccaga taacctaaga   2760
aacggttgtt tgacctttaa aggggtcaca acccacaggt ggagaactac tggtctaggg   2820
tcctttacag tcctttagct gcctcattta caggagataa catcatgctc aaaaactccc   2880
tccacatttg gctttttggg ttgttttgtt ttgtttttca agacagggtt tctctgtgta   2940
gccctggctg tcctggaact cacctttgta gaccaggctg gcctcgaact cagaaatccg   3000
cctgcttctg cctcctgagc gctgggatta aaggcgtgcg ccaccatgtc tggctcacat   3060
ctggcttttt aagagaccga ttttaacttc ttgcattgaa aataaatata gtagaaatgc   3120
ttaacctact aagacaataa aaacaggatt ccttctgcta ggaagaacac gttccagact   3180
aaggaaaaaa acctttttcag ggctttcatt acactgtgcc atgcactaat tttatgtttt   3240
cttcatcagt tttcagtgtc tgaaattcag tgtcaaaatt ctaagactac atatgatatc   3300
attacagtaa ctcagcaatt ctatgttacc agtaagtttt tctgtagttt aaaaaaaagg   3360
tggaagaaga aagcacagat agtttagcac atgggtaaaa tcagtaacta tttctgatga   3420
gcttggtgaa gatgctgtaa accatgcgac caccagtcct gttctctgtg ctttcagatg   3480
ttcgtcgtgg gtctgcttgg cctccttgca gctcctggtt ttgcttacgt aagtctcatt   3540
tttctgaagt tcattgtcaa aactgcattt acagtgaaat gtgatcttaa gtcaccctct   3600
gcttcttatg aacattagac ggtcaacatc aatggtaatg atggcaatgt agacggaagt   3660
ggacagcatt cggtgagcat caatggtgtg cacaacgtgg ccaatatcga caacaataac   3720
ggctgggact cctggaatag cctctgggac tatgaaaacg tatgtaatgg acacacaggg   3780
taaagatatg gtgtagccac cacccattaa aatttctgag gtgaattcta gctgttcatg   3840
aacattaaaa gctaccagta aaagtgccca ttccactcaa aacaatttta ctttttttgca   3900
tataattatt gctaataagt attacacaat aggtcgaaat tcaaagggat caatagtaag   3960
gataaaaact atgtacaaag acaaacacag catcctttgg tcttccctgc agagagtctc   4020
catgatgtta aaggtccaat gttttatgga ggctgaatga aatacgaatg cctctgtgat   4080
ggaaaaggcc caacatctta tggagaatga gtgaagtatg aatgctatta gttgtaagag   4140
aaggcgatgc aaagcaacac ttggcaccac ctgccaatta ctactttcct atttaaatgt   4200
agtttaaaaa gcaaagcctg tcttccctgc ctcctggaaa cactgcggat ggaggtagac   4260
caaggtatga cagcctttaa aagtttgtca gcaaaacact cccccataca cacatacaca   4320
caccctccta ctacactgga actgaagcaa aggcagtggg ttagatatat ccaccctcta   4380
agagtttgca ggtcatctat atatgatagc cagagacaca actgcaggac agccagactc   4440
tgagcactct ccccagctcc ttgtagctct gtttcagtgg tgacttgtga caagaatcct   4500
```

-continued

```
ggggaacctg tgcctcactg ttctctgtct tctttaatag agtttcgctg ccacgagact   4560
cttctccaag aagtcatgca ttgtgcacag aatgaacaag gatgccatgc cctcccttca   4620
ggacctcgat acaatggtca aggaacagaa ggtaaagtcc tgccttcttc tttggagtga   4680
caggaagtct tacagtctcc agtacacagt gaagtcaccc ccattccctc tttggtggag   4740
catgacagca tgtttgtcat gataaatgcc acaaacatgt aaaactgttc agtgtctgcc   4800
tgaatggagg gtggcttcca ctgtgtcaga tgccgtggcc cacatctgcc tctgcagggt   4860
ccagtaaagc actggctatc ttgagtgtca gagacccaaa ggtctgtaca cttcagtaca   4920
agccctccat atttcaaggg cacactccta cagtcgttgg ggttatcaga actagcaaac   4980
atagagactg gattttcaga tgaaaagaaa tcctttttaa agtctaagta tgccttatac   5040
aatgtttgag atattctcaa tactaaaaaa aaaaaaattg ttgcttgctt gaaaatcaaa   5100
tgtaaccaag tgtcctatat ccagtgtcaa tcatggctgt agtagatggg aagagggagc   5160
ccgtggtttt cacagtcaga cgcctgagtt attcttctaa gtgataaatt ggttcctata   5220
acaagcaagc cagtgaatat aaataagctc tatctcagaa gttatcctgt agtgctaccc   5280
tagaatctaa gagagcaaaa gtgcttcaaa tttcagaata agttttgctt tggacttctg   5340
tttttctaaa caactataac ttcaaaccat ctaagcctcg tgggacactt agaaatacca   5400
agccattcaa agctagaatt gtttcttcac cttacttgaa aacaaaatga caaccaaaaa   5460
ttgtccccac tgcccttgta catcttcaga tcagtaaagt cctgggctca gggatcattc   5520
actttctttc tttcctttca cactcaactt cagggtaaag ggcctggagg agctcctccc   5580
aaggacttga tgtactccgt caaccctacc agagtggagg acctgaatac attcggacca   5640
aagattgctg gcatgtgcag gggcatccct acctatgtgg ccgaggagat tccaggtgtg   5700
taccctgaga tgctgtatat cccaatgcag tactgagaga gccatcagac actctaaagt   5760
gtgaccacag acggaccaat catgtggatt atcagagcaa acacttgctt gctccttgtc   5820
agacagttgt ccatgcttca aaagttcatt aaaaaaaata gttcacaggc tcctcacaga   5880
aaccttagta gaatccacag cttctgctct tagtcttact ttttagaaac tgagacccag   5940
agaaaggtca caaaactttt gtctggctca ggttctatgt ctttaacttt atagaatacc   6000
gtctttctgg gtgggtgggc tctagagtaa acttcaagtg agttcaagga aagcatgaga   6060
agtagggaag accaaatgaa aggagaatgc caatgaaatc tatcgattct atagcgccaa   6120
tgcttaactc ctaggcgttc aaagaatagt atccacaagg tgtcagccta agatcctaat   6180
ctaacagcaa gttttcagat ctctgaagtg aaaagagaaa gcaagagagg aacagagaca   6240
gaaacagtaa gagacagaga ggcagagaca aagagacagg gagaatagag agggattaaa   6300
attaatatat agtttagaaa ttacgactcc tcacagtccc tgcagagtcc taggataggc   6360
actgatttgg acttcttttc ttctcactag gaccaaacca gcctttgtac tcaaagaagt   6420
gctacacagc tgacatactc tggattctgc ggatgtcctt ctgtggaaca tcagtggaga   6480
catactagaa gtcacaggaa aacaacccgt gggctctgac catcgcaatg cttgattatg   6540
agagtgttct ctgggggttg tgattagctt ctttaaggct caataaaccc acgtggcagc   6600
acatccagtt tgtaatgaca tgcctcatga cttctatggg agtccaatgt ggcacctgcc   6660
agcctgtatt caggacctct ccgctataaa gcatccctcc agagttttca aatactacaa   6720
agcacagcct gggtttgggc tcagataggc cactgctgcc tgactacatt acagacaaac   6780
aagttttaaa agaaagaaaa aagagctcag agtggctgga atcagcaagg gtgtttttcc   6840
```

-continued

```
tgcaaggagc cagaagtatc aataatcacc caaggaggag acactgggaa tgagagacta   6900

gaacacacgc ctgcagatac ggagaacctc agcattgccg ctctctccca taactgcaca   6960

ccccttctg taaactctgc ttctttcttt cacctgaaga tggcccttgc ttttttttat   7020

tataggacan gataactaga ccagaaagtc aacctgactc tctacattta tatgtcttcc   7080

cagntcaaga aatattattt actggtgaat ggcacttcta tattcccttg gttcaataag   7140

tctacaggat ccattcattg acaggccaag agtgagatca catgataccc aagcacatgg   7200

gtctttcctt gaaggagaag gatcca                                        7226
```

<210> SEQ ID NO 5
<211> LENGTH: 543
<212> TYPE: DNA
<213> ORGANISM: Mus sp.

<400> SEQUENCE: 5

```
atgttcgtcg tgggtctgct tggcctcctt gcagctcctg gttttgctta cacggtcaac     60

atcaatggta atgatggcaa tgtagacgga agtggacagc attcggtgag catcaatggt    120

gtgcacaacg tggccaatat cgacaacaat aacggctggg actcctggaa tagcctctgg    180

gactatgaaa acagtttcgc tgccacgaga ctcttctcca agaagtcatg cattgtgcac    240

agaatgaaca aggatgccat gccctccctt caggacctcg atacaatggt caaggaacag    300

aagggtaaag ggcctggagg agctcctccc aaggacttga tgtactccgt caaccctacc    360

agagtggagg acctgaatac attcggacca aagattgctg gcatgtgcag ggcatccct    420

acctatgtgg ccgaggagat tccaggacca aaccagcctt tgtactcaaa gaagtgctac    480

acagctgaca tactctggat tctgcggatg tccttttgtg gaacatcagt ggagacatac    540

tag                                                                  543
```

<210> SEQ ID NO 6
<211> LENGTH: 184
<212> TYPE: PRT
<213> ORGANISM: Mus sp.

<400> SEQUENCE: 6

```
Met Lys Leu Thr Met Phe Val Val Gly Leu Leu Gly Leu Leu Ala Ala
  1               5                  10                  15

Pro Gly Phe Ala Tyr Thr Val Asn Ile Asn Gly Asn Asp Gly Asn Val
             20                  25                  30

Asp Gly Ser Gly Gln Gln Ser Val Ser Ile Asn Gly Val His Asn Val
         35                  40                  45

Ala Asn Ile Asp Asn Asn Asn Gly Trp Asp Ser Trp Asn Ser Leu Trp
     50                  55                  60

Asp Tyr Glu Asn Ser Phe Ala Ala Thr Arg Leu Phe Ser Lys Lys Ser
 65                  70                  75                  80

Cys Ile Val His Arg Met Asn Lys Asp Ala Met Pro Ser Leu Gln Asp
                 85                  90                  95

Leu Asp Thr Met Val Lys Glu Gln Lys Gly Lys Gly Pro Gly Gly Ala
            100                 105                 110

Pro Pro Lys Asp Leu Met Tyr Ser Val Asn Pro Thr Arg Val Glu Asp
        115                 120                 125

Leu Asn Thr Phe Gly Pro Lys Ile Ala Gly Met Cys Arg Gly Ile Pro
    130                 135                 140

Thr Tyr Val Ala Glu Glu Ile Pro Gly Pro Asn Gln Pro Leu Tyr Ser
145                 150                 155                 160
```

-continued

```
Lys Lys Cys Tyr Thr Ala Asp Ile Leu Trp Ile Leu Arg Met Ser Phe
                165                 170                 175

Cys Gly Thr Ser Val Glu Thr Tyr
            180


<210> SEQ ID NO 7
<211> LENGTH: 597
<212> TYPE: DNA
<213> ORGANISM: Sus scrofa

<400> SEQUENCE: 7

atgcctgact tctcacttca ttgcattggt gaagccaaga tgaagttcac aattgccttt      60

gctggacttc ttggtgtctt cctgactcct gcccttgctg actatagtat cagtgtcaac     120

gacgacggca acagtggtgg aagtgggcag cagtcagtga gtgtcaacaa tgaacacaac     180

gtggccaacg ttgacaataa caatggatgg aactcctgga atgccctctg ggactataga     240

actggctttg ctgtaaccag actcttcgag aagaagtcat gcattgtgca caaaatgaag     300

aaggaagcca tgccctccct tcaagccctt gatgcgctgg tcaaggaaaa gaagcttcag     360

ggtaagggcc caggggggacc acctcccaag agcctgaggt actcagtcaa ccccaacaga     420

gtcgacaacc tggacaagtt tggaaaatcc atcgttgcca tgtgcaaggg gattccaaca     480

tacatggctg aagagattca aggagcaaac ctgatttcgt actcagaaaa gtgcatcagt     540

gccaatatac tctggattct taacatttcc ttctgtggag gaatagcgga gaactaa        597


<210> SEQ ID NO 8
<211> LENGTH: 185
<212> TYPE: PRT
<213> ORGANISM: Sus scrofa

<400> SEQUENCE: 8

Met Lys Phe Thr Ile Ala Phe Ala Gly Leu Leu Gly Val Phe Leu Thr
  1               5                  10                  15

Pro Ala Leu Ala Asp Tyr Ser Ile Ser Val Asn Asp Asp Gly Asn Ser
            20                  25                  30

Gly Gly Ser Gly Gln Gln Ser Val Ser Val Asn Asn Glu His Asn Val
        35                  40                  45

Ala Asn Val Asp Asn Asn Asn Gly Trp Asn Ser Trp Asn Ala Leu Trp
    50                  55                  60

Asp Tyr Arg Thr Gly Phe Ala Val Thr Arg Leu Phe Glu Lys Lys Ser
 65                  70                  75                  80

Cys Ile Val His Lys Met Lys Lys Glu Ala Met Pro Ser Leu Gln Ala
                85                  90                  95

Leu Asp Ala Leu Val Lys Glu Lys Lys Leu Gln Gly Lys Gly Pro Gly
            100                 105                 110

Gly Pro Pro Pro Lys Ser Leu Arg Tyr Ser Val Asn Pro Asn Arg Val
        115                 120                 125

Asp Asn Leu Asp Lys Phe Gly Lys Ser Ile Val Ala Met Cys Lys Gly
    130                 135                 140

Ile Pro Thr Tyr Met Ala Glu Glu Ile Gln Gly Ala Asn Leu Ile Ser
145                 150                 155                 160

Tyr Ser Glu Lys Cys Ile Ser Ala Asn Ile Leu Trp Ile Leu Asn Ile
                165                 170                 175

Ser Phe Cys Gly Gly Ile Ala Glu Asn
            180                 185
```

-continued

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Met Arg Gly Ser His His His His His His Gly Ser
1 5 10

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Consensus
sequence
<220> FEATURE:
<221> NAME/KEY: MOD_RES
<222> LOCATION: (4)
<223> OTHER INFORMATION: Lys or Gln
<220> FEATURE:
<221> NAME/KEY: MOD_RES
<222> LOCATION: (6)
<223> OTHER INFORMATION: Leu or deleted
<220> FEATURE:
<221> NAME/KEY: MOD_RES
<222> LOCATION: (7)
<223> OTHER INFORMATION: Gln or deleted
<220> FEATURE:
<221> NAME/KEY: MOD_RES
<222> LOCATION: (14)
<223> OTHER INFORMATION: Pro or Ala

<400> SEQUENCE: 10

Val Lys Glu Xaa Lys Xaa Xaa Gly Lys Gly Pro Gly Gly Xaa Pro Pro
1 5 10 15

Lys

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Lys Lys Leu Gln Gly Lys Gly Pro Gly Gly Pro Pro Pro Lys
1 5 10

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Leu Asp Ala Leu Val Lys Glu Lys Lys Leu Gln Gly Lys Gly Pro Gly
1 5 10 15

Gly Pro Pro Pro Lys
20

<210> SEQ ID NO 13

-continued

<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Leu Asp Ala Leu Val Lys Glu Lys Lys Leu Gln Gly Lys Gly Pro Gly
  1               5                  10                  15

Gly Pro Pro Pro Lys Gly Leu Met Tyr
             20                  25
```

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Lys Lys Thr Cys Ile Val His Lys Met Lys Lys
  1               5                  10
```

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Lys Lys Glu Val Met Pro Ser Ile Gln Ser Leu Asp Ala Leu Val Lys
  1               5                  10                  15

Glu Lys Lys
```

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: 6-His tag

<400> SEQUENCE: 16

```
His His His His His His
  1               5
```

<210> SEQ ID NO 17
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Lys Lys Thr Cys Ile Val His Lys Met Lys Lys Glu Val Met Pro Ser
  1               5                  10                  15

Ile Gln Ser Leu Asp Ala Leu Val Lys Glu Lys Lys Leu Gln Gly Lys
             20                  25                  30

Gly Pro Gly Gly Pro Pro Pro Lys Gly Leu
         35                  40
```

-continued

```
<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Lys Leu Gln Gly Lys Gly Pro Gly Gly Pro Pro Pro Lys Gly Leu
  1               5                  10                  15

Met Tyr


<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Lys Pro Leu Gly Gln Pro Gly Lys Val Pro Lys Leu Asp Gly Lys
  1               5                  10                  15

Glu Pro Leu Ala Lys
             20


<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Gly Pro Gly Gly Pro Pro Pro Lys
  1               5


<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Lys Leu Gln Gly Lys
  1               5


<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Pro Gly Gly
  1


<210> SEQ ID NO 23
<211> LENGTH: 23
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 23

Leu Asp Thr Met Val Lys Glu Gln Lys Gly Lys Gly Pro Gly Gly Ala
  1               5                  10                  15

Pro Pro Lys Asp Leu Met Tyr
             20


<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:
      Glycine-proline synthetic peptide

<400> SEQUENCE: 24

Gly Pro Gly Gly Pro Pro Pro
  1               5


<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Lys or Gln
<220> FEATURE:
<221> NAME/KEY: MOD_RES
<222> LOCATION: (14)
<223> OTHER INFORMATION: Pro or Ala

<400> SEQUENCE: 25

Val Lys Glu Xaa Lys Leu Gln Gly Lys Gly Pro Gly Gly Xaa Pro Pro
  1               5                  10                  15

Lys


<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Lys or Gln
<220> FEATURE:
<221> NAME/KEY: MOD_RES
<222> LOCATION: (12)
<223> OTHER INFORMATION: Pro or Ala

<400> SEQUENCE: 26

Val Lys Glu Xaa Lys Gly Lys Gly Pro Gly Gly Xaa Pro Pro Lys
  1               5                  10                  15
```